(12) United States Patent
Oba et al.

(10) Patent No.: US 8,491,157 B2
(45) Date of Patent: Jul. 23, 2013

(54) ILLUMINATING DEVICE AND METHOD FOR MANUFACTURING THEREOF

(75) Inventors: Hitoshi Oba, Kameoka (JP); Naoki Nishimori, Kusatsu (JP); Akira Matsui, Joyo (JP); Nobuharu Ishikawa, Takatsuki (JP); Yoshihiro Yamashita, Fukuchiyama (JP); Takahiro Suga, Joyo (JP); Kosuke Sugiyama, Nantan (JP)

(73) Assignee: OMRON Corporation, Kyoto-shi (JP)

( * ) Notice: Subject to any disclaimer, the term of this patent is extended or adjusted under 35 U.S.C. 154(b) by 170 days.

(21) Appl. No.: 13/044,819

(22) Filed: Mar. 10, 2011

(65) Prior Publication Data

US 2011/0222286 A1 Sep. 15, 2011

(30) Foreign Application Priority Data

Mar. 12, 2010 (JP) ................................. 2010-055402
Feb. 2, 2011 (JP) ................................. 2011-020892

(51) Int. Cl.
*F21S 8/00* (2006.01)

(52) U.S. Cl.
USPC .......................................... 362/268; 362/800

(58) Field of Classification Search
USPC ........................ 362/268, 800; 257/98, 99, 100
See application file for complete search history.

(56) References Cited

U.S. PATENT DOCUMENTS

| 5,031,198 | A | * | 7/1991 | Deucher et al. | .................... 378/4 |
| 8,206,023 | B2 | * | 6/2012 | Kang et al. | ..................... 362/632 |
| 8,240,882 | B2 | * | 8/2012 | Liao et al. | ................ 362/249.02 |
| 8,262,250 | B2 | * | 9/2012 | Li et al. | .......................... 362/219 |
| 2008/0249363 | A1 | * | 10/2008 | Nakamura et al. | ............. 600/132 |
| 2009/0303426 | A1 | * | 12/2009 | Kim | .............................. 349/150 |

FOREIGN PATENT DOCUMENTS

| JP | 2000-269549 A | 9/2000 |
| JP | 2002-083506 A | 3/2002 |
| JP | 2002-184209 A | 6/2002 |
| JP | 2008-139708 A | 6/2008 |
| JP | 2009-146841 A | 7/2009 |

* cited by examiner

*Primary Examiner* — Jong-Suk (James) Lee
*Assistant Examiner* — Mark Tsidulko
(74) *Attorney, Agent, or Firm* — Marvin A. Motsenbocker; Mots Law, PLLC

(57) ABSTRACT

To provide a method for manufacturing a plurality of types of illuminating devices having different specifications while reducing cost. A substrate includes a common flexible portion and a plurality of units bendable with respect to the common portion, where the common portion includes a pad that is extended in the horizontal direction in the plane of the drawing and that is arranged for every predefined interval. In the present manufacturing method, a substrate piece is created by cutting the substrate mounted with the light emitting element in a first direction, the common portion in the substrate piece is formed according to the illuminating device to be manufactured, the relative position of the individual portion with respect to the formed common portion is respectively positioned, and the wiring for supplying power to the pad in the substrate piece is formed.

18 Claims, 36 Drawing Sheets

ILLUMINATION RANGE 1    ILLUMINATION RANGE 2

ILLUMINATION RANGE 1    ILLUMINATION RANGE 2    ILLUMINATION RANGE 2

ILLUMINATION RANGE          ILLUMINATION RANGE

ILLUMINATING DEVICE AND METHOD FOR MANUFACTURING THEREOF

CROSS REFERENCE TO RELATED APPLICATIONS

This application claims priority based on 35 USC 119 from prior Japanese Patent Application No. 2010-055402 filed on Mar. 12, 2010, and Japanese Patent Application No. 2011-020892 filed on Feb. 2, 2011, entitled "ILLUMINATING DEVICE" and the entire contents of which are incorporated herein by reference.

BACKGROUND OF THE INVENTION

1. Technical Field

The present invention relates to an illuminating device including a light emitting element, a method of manufacturing the same, and an illuminating device. In particular, the present invention relates to a ring-shaped illuminating device for illuminating an object to be imaged when acquiring an image.

2. Related Art

In the field of FA (Factory Automation) and the like, various types of image processing techniques are being used. Typically, an image processing technique for recognizing characters printed on an object to be examined, and examining for the presence of scratches on a surface of the object to be examined and the like, based on the image data obtained by imaging the object to be examined, is being widely put to practical use.

When performing various types of measurement processes on the object to be examined using such image processing technique, the image representing the object to be examined needs to be appropriately acquired. For this reason, an illuminating device for illuminating the object to be examined is often arranged to ensure appropriate illumination at the time of imaging. As the illuminating device described above, an illuminating device using a light emitting element (LED: Light Emitting Diode) having low power consumption and long lifespan is put to practical use.

In the illuminating device using such a light emitting element, a configuration using a so-called chip LED is adopted in place of a conventional shell type LED.

For example, Japanese Unexamined Patent Publication No. 2002-184209 discloses an LED illuminating device including a flexible printed circuit substrate held in a predetermined stereoscopic shape, and a large number of light emitting diode elements directly attached to the flexible printed circuit substrate according to a predetermined pattern.

Japanese Unexamined Patent Publication No. 2002-83506 discloses an illuminating device in which a light emitting unit with a flexible substrate and a large number of light emitting diodes mounted on one surface of the flexible substrate is arranged in a case. In such an illuminating device, the configuration of arranging in the case with the other surface of the flexible substrate not mounted with the light emitting diode and the inner surface of a main body facing each other is adopted.

Japanese Unexamined Patent Publication No. 2000-269549 discloses an illuminating device capable of achieving uniform illumination effect over a wide area with respect to the object to be illuminated having an elongate shape.

In the ring-shaped illuminating device disclosed in Japanese Unexamined Patent Publication No. 2008-139708, a plurality of LED columns are concentrically arranged and a plurality of optical members are concentrically arranged in correspondence with respective LED columns so that illumination modes on a workpiece by the respective LED columns differ from each other, and respective additional optical members are arranged to realize an integrated structure. A single device thus can support a plurality of types of objective lenses and workpieces.

In an LED illuminating device disclosed in Japanese Unexamined Patent Publication No. 2009-146841, positioning pins arranged on a flat base portion are inserted to through-holes formed in a flat LED substrate mounted with a plurality of LEDs and positioning pin insertion holes formed in an integrated lens holder for holing a plurality of lenses to position the lens holder with respect to the LED substrate. The individual lens thus can be positioned with respect to each of the plurality of LEDs.

SUMMARY

In the image processing technique in the FA field described above, a wide variety of objects to be examined need to be measured. For example, the objects to be examined cover a wide range from a compact electronic component to a completed product such as an automobile. Thus, a great number of variations (product groups) for the illumination field and the illumination distance (installation distance: work distance) are preferably available with respect to the illuminating device to respond to a wide variety of applications.

A light emitting element and a lens for optical path control are preferably combined to provide a large number of variations (product groups).

A ring shape in which the light emitting elements are concentrically arranged at the periphery of the center hole is frequently adopted for the shape of the illuminating device. With this ring shape, the workpiece can be uniformly irradiated with light and more accurate imaging can be carried out.

In such ring-shaped illuminating device, however, attachment needs to be such that the optical axis of each light emitting element that directs light toward the workpiece positioned on the axis of the center hole is inclined with respect to the axis of the center hole.

However, the illuminating devices of Japanese Unexamined Patent Publication Nos. 2002-184209 and 2002-83506 are not directed to image processing in the FA field in the first place. Thus, the flexible substrate accommodate the number of product groups in order to achieve the large number of variations of the illumination field and the illumination distance in the illuminating device of Japanese Unexamined Patent Publication No. 2002-184209, which causes increase in cost. The illuminating device of Japanese Unexamined Patent Publication No. 2002-83506 has a similar problem.

In the illuminating device of Japanese Unexamined Patent Publication No. 2000-269549, such ring-shaped illuminating device cannot be realized.

In the illuminating device disclosed in Japanese Unexamined Patent Publication No. 2008-139708, the lens must accommodate the variation of the field and the work distance, which causes increase in cost. In the illuminating device disclosed in Japanese Unexamined Patent Publication No. 2009-146841, the variation that can be achieved for the field and the work distance is limited since the light emitting element and the lens cannot be inclined. Furthermore, the lens may drop toward the workpiece since the lens is arranged on the side of the light irradiation surface with respect to the lens holder, and hence it is not suitable for a visual sensor illuminating device for FA.

The present invention has been devised to alleviates the problems described above, and an object thereof is to provide a ring-shaped illuminating device capable of accommodating different specifications while reducing cost increase and lowering of reliability. Another object of the present invention is to provide a method capable of manufacturing a plurality of types of illuminating devices having different specifications while reducing increase in cost. Still another object of the present invention is to provide an illuminating device capable of accommodating different specifications while reducing increase in cost.

In accordance with one aspect of the present invention, an illuminating device configured by shaping a substrate mounted with a plurality of light emitting elements is provided. The substrate includes a first portion having a shape extending in a first direction and being flexible, and a plurality of second portions made from a second material harder than that of the first portion and each extending in a direction different from the first direction. Each second portion is mounted with at least one light emitting element. The substrate further includes wiring for connecting the plurality of light emitting elements of the first portion and the plurality of second portions. The first portion is formed in a predefined direction and size according to the illuminating device; and each of the second portions is positioned according to an irradiating direction of the light emitting element being mounted.

The first portion is preferably concentrically formed along the first direction; and each second portion is preferably folded in a concentric axial direction defined by the first portion.

The folding is more preferably carried out at a connecting portion of the second portion and the first portion. The second portion is preferably mounted with a chip LED.

The second portion is preferably made of glass epoxy.

In accordance with another aspect of the present invention, a method for manufacturing an illuminating device including a light emitting element is provided. The manufacturing method includes a step of creating a substrate piece that cuts a substrate mounted with the light emitting element in a first direction to create a substrate piece. The substrate includes a first flexible portion, and a plurality of second portions that can be bent with respect to the first portion, where the first portion includes a pad extending in a second direction orthogonal to the first direction and being arranged for every predefined interval in the second direction. Each second portion is connected to the first portion between two continuous pads and includes wiring for electrically connecting the terminal of the mounted light emitting element to the two corresponding pads. The manufacturing method also includes steps of forming the first portion of the substrate piece according to the illuminating device to be manufactured, positioning the relative position of the second portion with respect to the formed first portion, and forming wiring for supplying power to the pad arranged in the substrate piece.

In the step of creating the substrate piece, the cutting length is preferably changed according to the shape of the illuminating device to be manufactured.

In the step of creating the substrate piece, the substrate is more preferably cut in the first direction at the position where the pad exists.

In the forming step, the first portion is more preferably formed in a ring shape.

The first and second portions are preferably both flexible printed substrates.

The first portion is preferably a flexible printed substrate, and the second potion preferably includes a glass epoxy substrate.

A plurality of substrate pieces are preferably created in the step of creating the substrate piece, and the first portions of the plurality of created substrate pieces are preferably formed in the forming step respectively. The manufacturing method further includes a step of fixing the plurality of formed substrate pieces at predefined positional relationship.

At the second portion, the wiring is preferably formed so that the plurality of light emitting elements can be mounted in series and wiring for by-passing the light emitting element positioned in the middle when connected in series and the corresponding pad is preferably formed, where the substrate is cut in the first direction, one part of the second portion in the substrate piece obtained by cutting is cut in the second direction and the cut wiring is electrically connected to the corresponding pad in the step of creating the substrate piece.

In accordance with still another aspect of the present invention, an illuminating device including a light emitting element is provided. The illuminating device includes a substrate piece on which a light emitting element is mounted and including a pad to be electrically connected with the light emitting element, and a circuit for supplying power to the pad. The substrate piece is obtained by cutting a substrate in a first direction, the substrate including a first flexible portion and a plurality of second portions that can be bent with respect to the first portion. The first portion includes a pad extending in a second direction orthogonal to the first direction and being arranged for every predefined interval in the second direction. Each second portion is connected to the first portion between two continuous pads and includes wiring for electrically connecting the terminal of the mounted light emitting element to the two corresponding pads. The first portion is formed according to the illuminating device. The second portion is positioned according to the irradiating direction of the light emitting element with respect to the first portion.

A unit for changing the relative position of the second portion with respect to the first portion is further preferably arranged.

According to the present invention, a plurality of types of illuminating devices having different specifications can be provided while reducing increase in cost.

DETAILED DESCRIPTION

Figure 1:
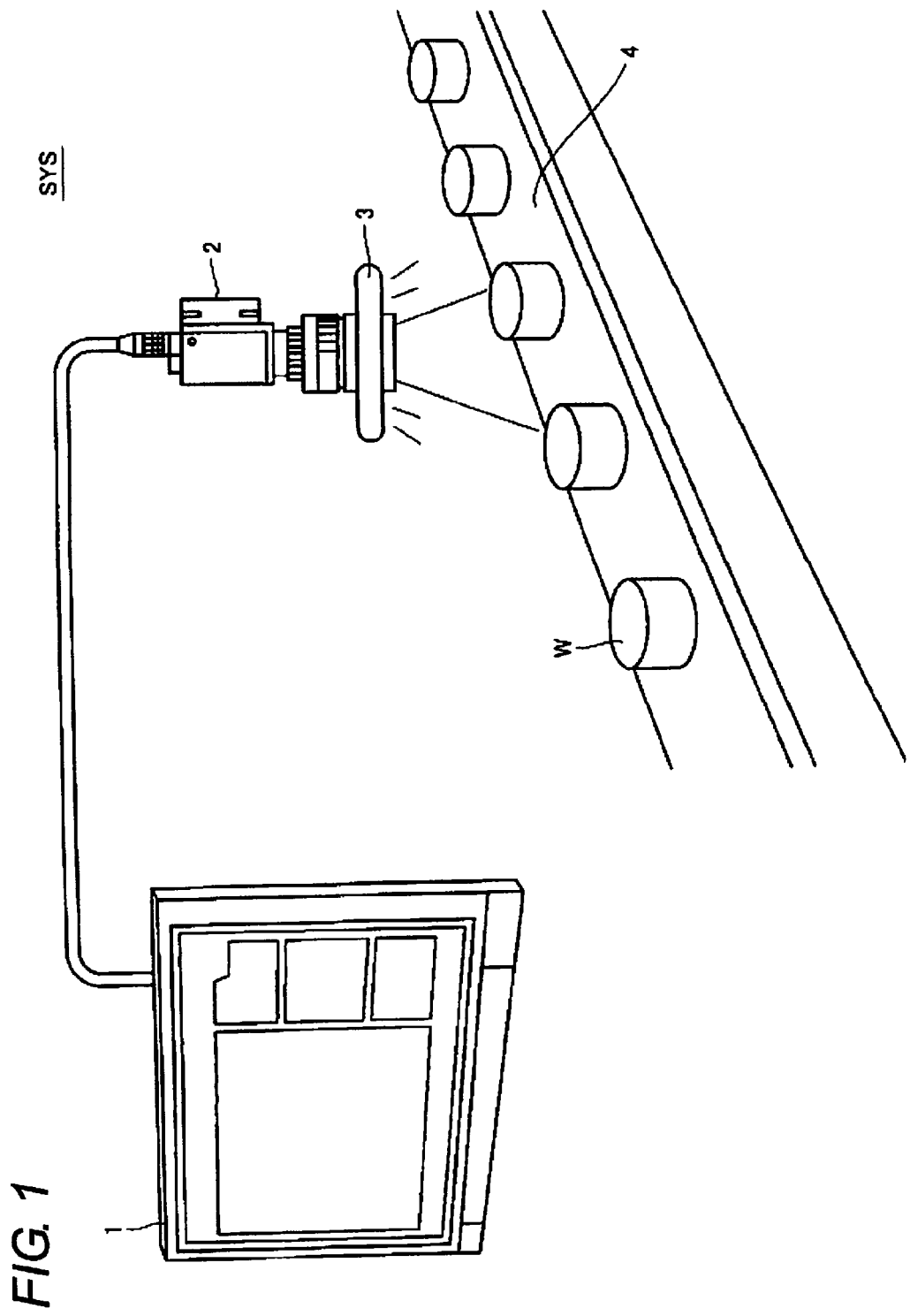
FIG. 1 is a schematic view showing an outline of a visual sensor system using an illuminating device according to the present embodiment.

Hereinafter, preferred embodiments of the present invention will be described with reference to the drawings. Like reference numerals are used to designate like or corresponding portions throughout the figures, and the description thereof will not be repeated.

A. Outline

A method for manufacturing an illuminating device according to the present embodiment is used to manufacture a plurality of types of illuminating device having different size and specifications using a common substrate on which a light emitting element is to be mounted. The substrate is typically in a state of being wound around a reel, as hereinafter described, and is cut into a necessary length to create a substrate piece in a manufacturing process according to the size, specification, and the like of the illuminating device to be manufactured. The illuminating device is manufactured using the substrate piece. Therefore, a large number of variations (product groups) for the illumination field and the illumination distance can be accommodated using the common substrate.

B. Overall Structure

FIG. 1 is a schematic view showing the outline of a visual sensor system SYS using the illuminating device according to the present embodiment. With reference to FIG. 1, the visual sensor system SYS is typically incorporated in a production line and the like, and executes a process (hereinafter also referred to as a "measurement process") such as character recognition and scratch examination based on an image obtained by imaging an object to be examined (hereinafter also referred to as a "workpiece") W.

More specifically, the visual sensor system SYS includes an image processing device 1, a camera 2 connected to the image processing device 1, and an illuminating device 3 (in the following description, illuminating devices 3A to 3H are illustrated apart from the present embodiment) for illuminating the field range and the vicinity of the camera 2. The camera 2 images the workpiece W transported on the production line 4 at an appropriate timing to generate image data, and outputs the generated image data to the image processing device 1. The image processing device 1 is a computer including a CPU (Central Processing Unit), a memory, and the like, and is integrally formed with a display for displaying measurement processing results and the like in the example shown in FIG. 1.

The illuminating device 3 according to the present embodiment uses a light emitting element such as LED (Light Emitting Diode) as a light source. The LED serving as a light source of the illuminating device 3 may be a shell type LED, a surface mounting chip LED, a bare chip mounting LED, and the like depending on the difference in shape, mounting mode and the like. In particular, the illuminating device according to the present embodiment is suitable when using the surface mounting chip LED or the bare chip mounting LED.

Although FIG. 1 shows a configuration in which a ring-shaped (doughnut-shaped) illuminating device is attached to the periphery of the camera 2, an illuminating device arranged in the vicinity of the camera 2 may be adopted. In this case, the shape (outer shape, size, etc. of the light emitting portion) of the illuminating device also can be designed according to the application.

C. Illuminating Device

The range of types of illuminating devices that can be manufactured with the manufacturing method according to the present embodiment will now be described. FIGS. 2 to 9 are views showing the outer appearance of the illuminating device according to the present embodiment.

[c1. Direct Ring Type]

Figure 2:
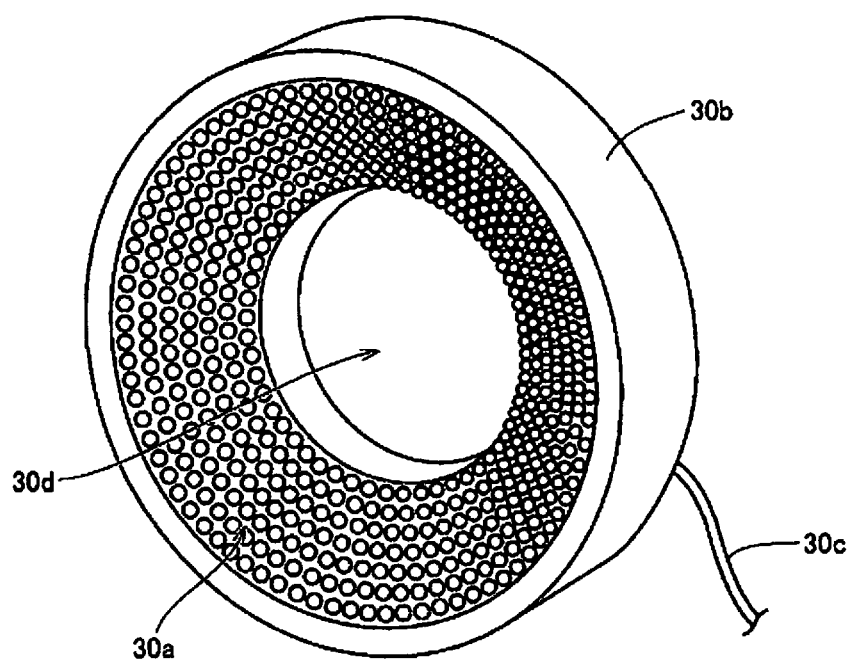
FIG. 2 is a view showing an outer appearance of the illuminating device according to the present embodiment.

FIG. 2 shows a direct ring type illuminating device 3A as one example of the illuminating device according to the present embodiment. Illuminating device 3A has a bowl shape, where a plurality of light emitting elements 30a are arranged on the inner surface of a housing 30b having a circular void portion 30d formed at the center part. More specifically, the inner surface of housing 30b is formed to be inclined toward the center part, and the light emitting elements 30a are arranged in a line at predetermined intervals on the inclined inner surface. The void portion 30d is a hole for the camera 2 to pass through to be arranged as shown in FIG. 1.

The power for turning ON the light emitting element 30a is supplied by a supply line 30c. The all light emitting elements 30a may be turned ON/OFF all together, but the light emitting elements 30a on each circumference arranged in order from the center part toward the outer periphery may be independently driven. In other words, one group of light emitting elements 30a arranged on the circumference positioned on the inner periphery side and one group of light emitting elements 30a arranged on the circumference positioned on the outer periphery side may be respectively turned ON/driven at independent times to more uniformly illuminate the workpiece W.

[c2. Dome Type]

Figure 3:
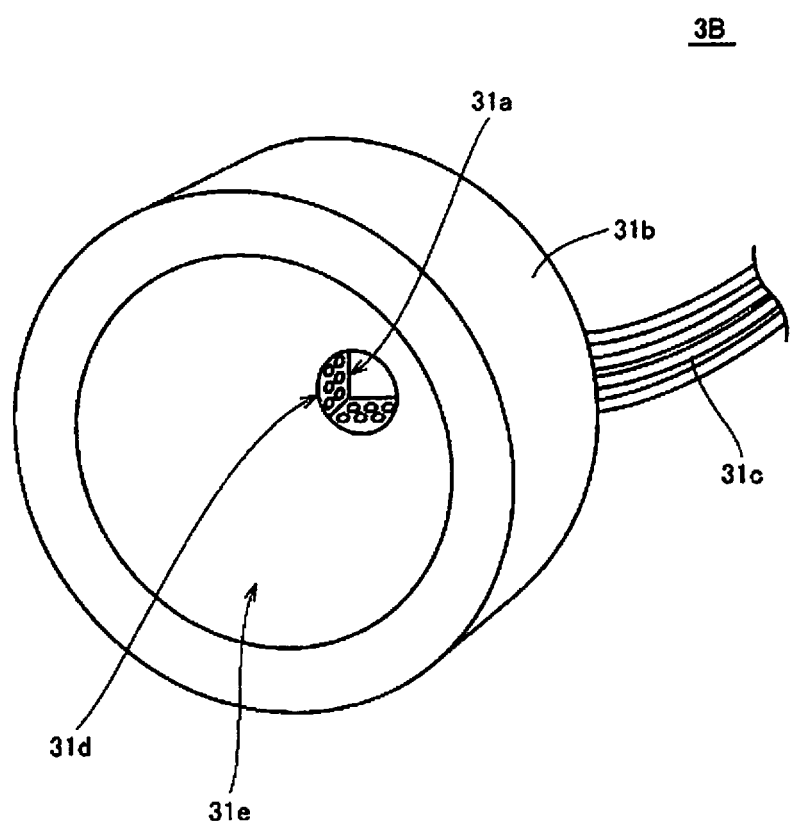
FIG. 3 is a view showing an outer appearance of the illuminating device according to the present embodiment.

FIG. 3 shows a dome type illuminating device 3B as one example of the illuminating device according to the present embodiment. In illuminating device 3B, light emitting elements 31a are arranged at the lower part in the dome (bottom of inner surface side) of a housing 31b the inner surface of which has a dome (semispherical) shape. More specifically, a storage space 31d for storing the light emitting elements 31a is formed at the lower part in the dome of housing 31b, and the light emitting elements 31a are arranged over the entire periphery of storage space 31d. The light emitted from light emitting elements 31a is diffusely reflected at a diffuse reflection surface 31e formed on the inner surface of housing 31b, and then incident on the workpiece. The power for lighting such light emitting elements 31a is supplied by a supply line 31c.

[c3. Square Oblique Light Type]

Figure 4:
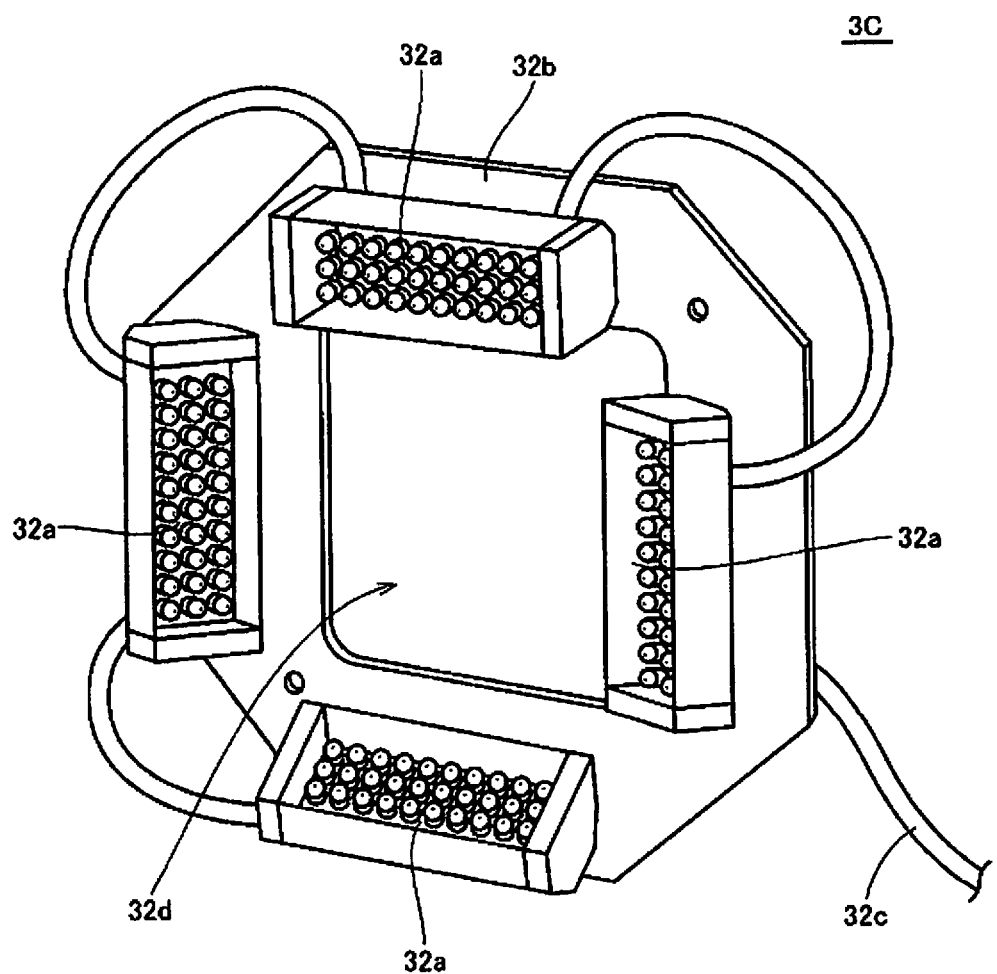
FIG. 4 is a view showing an outer appearance of the illuminating device according to the present embodiment.

FIG. 4 shows a square oblique type illuminating device 3C as one example of the illuminating device according to the present embodiment. The illuminating device 3C has light emitting units arranged on an octagonal base plate 32b in which four square corners are cutout, where the light emitting units have light emitting elements 32a arranged in a line at positions corresponding to four sides of the square. A substantially square void portion 32d is formed at the center portion of the base plate 32b. The camera 2 may pass through and be arranged at the void portion 32d.

Each light emitting unit is arranged so as to face the center portion of the base plate 32b. In this arrangement, the workpiece W arranged on a center axis of the base plate 32b can be irradiated with the light emitted from each light emitting element 32a.

The power for lighting the light emitting elements 32a is supplied by a supply line 32c. The all light emitting elements may be turned ON/OFF all together, but may be independently driven in units of light emitting units. The workpiece W then can be more uniformly illuminated.

[c4. Bar/Line Type]

Figure 5:
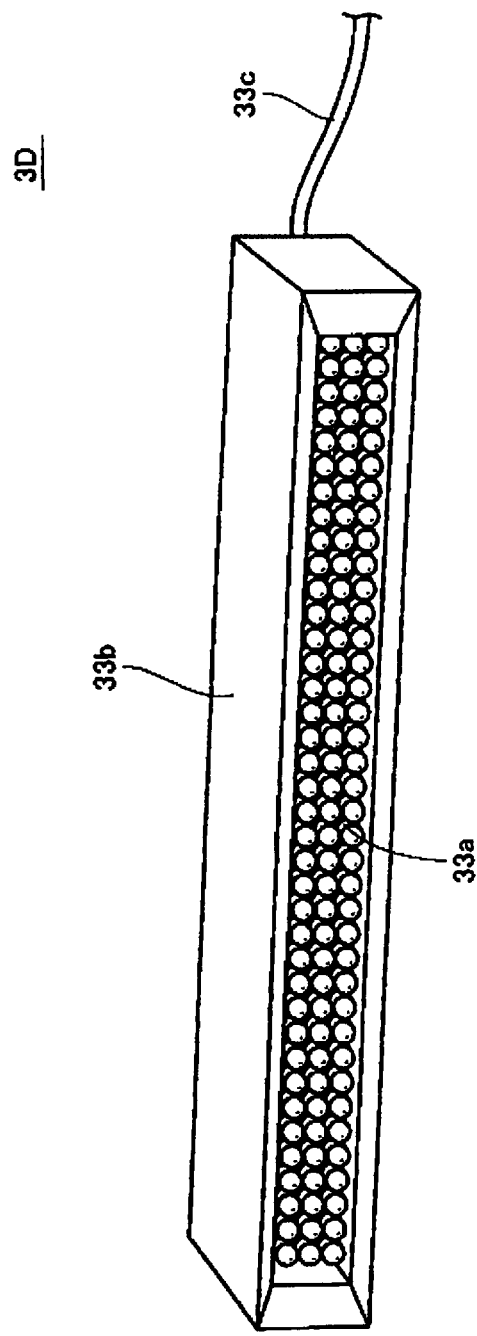
FIG. 5 is a view showing an outer appearance of the illuminating device according to the present embodiment.

FIG. 5 shows a bar/line type illuminating device 3D as one example of the illuminating device according to the present embodiment. Illuminating device 3D has a plurality of light emitting elements 33a arranged in a line in a predetermined direction in a rectangular housing 33b. An example in which the light emitting elements 33a are arranged in a line of three columns is shown in FIG. 5, but may be arranged in one column or two columns, or the light emitting elements 33a may be arranged in a line over a greater number of columns. The bar/line type illuminating device 3D is typically arranged such that the longitudinal direction thereof is parallel to or perpendicular to the transporting direction of the production line 4.

The power for lighting the light emitting elements 33a is supplied by a supply line 33c. The all light emitting elements 33a may be turned ON/OFF all together, but may be independently driven in units of columns. The workpiece W then can be more uniformly illuminated.

[c5. Directly Below Type]

Figure 6:
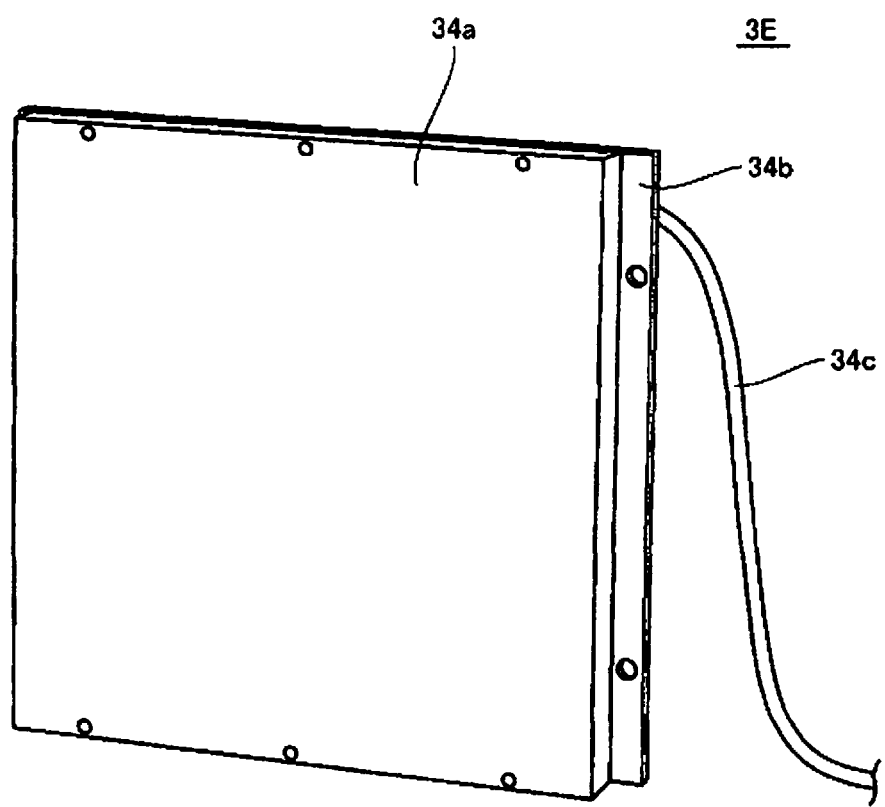
FIG. 6 is a view showing an outer appearance of the illuminating device according to the present embodiment.

FIG. 6 shows a directly below type illuminating device 3E as one example of the illuminating device according to the present embodiment. Illuminating device 3E has a plurality of light emitting elements (not shown) arranged in a line on the surface of a substantially square housing 34b, and a diffusion transmission unit 34a is arranged to cover the light emitting surfaces of the light emitting elements. The light emitted from the plurality of light emitting elements is thus diffused by the diffusion transmission unit 34a to illuminate the workpiece. The power for lighting the light emitting elements is supplied by a supply line 34c.

[c6. Ring Type]

Figure 7A:
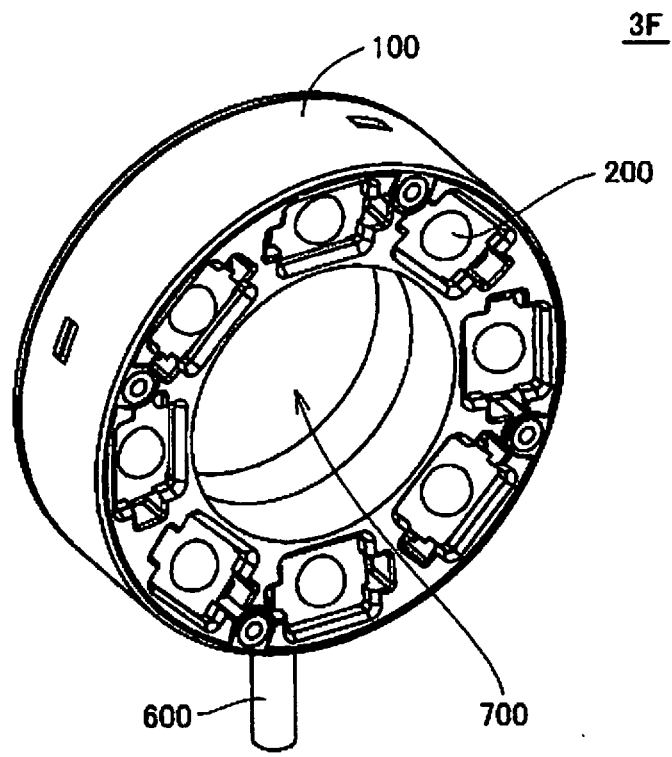
FIGS. 7A and 7B are views showing an outer appearance of the illuminating device according to the present embodiment.
Figure 7B:
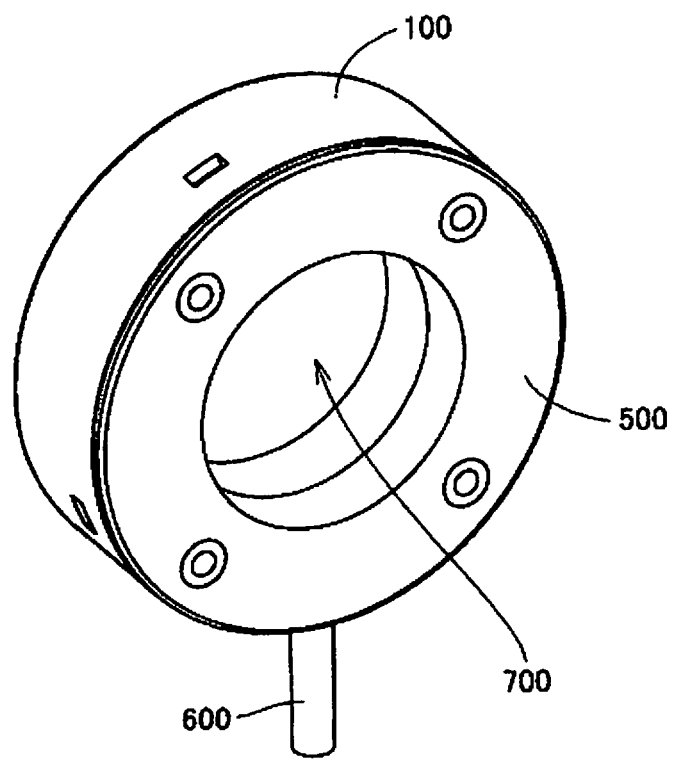

FIGS. 7A and 7B show a ring type illuminating device 3F mounted with eight LEDs as one example of the illuminating device according to the present embodiment. FIG. 7A shows the irradiation surface side of illuminating device 3F, and FIG. 7B shows the rear surface side of illuminating device 3F.

As shown in FIGS. 7A and 7B, illuminating device 3F has a ring shape as a whole. More specifically, illuminating device 3F includes a base 100 corresponding to a first housing, and a case 500 corresponding to a second housing. As hereinafter described, the base 100 and the case 500 are configured as an integrated ring shape by being fitted to each other by snap-fit and the like.

A plurality of lenses 200 are concentrically arranged on the irradiation surface of the base 100. The irradiation surface of base 100 is formed as an inclined surface having a predetermined angle with respect to a center axis of center hole 700 formed to pass through the base 100 and the case 500.

A unit substrate mounted with light emitting elements corresponding to the respective lenses 200 is arranged in case 500, and a power supply cable 600 for supplying power to the light emitting elements is attached through a cutout formed at the side surface of case 500.

The illuminating device 3F in which eight lenses are attached on the irradiation surface is illustrated in FIGS. 7A and 7B, but instead of such a configuration, a configuration in which a greater number of lenses or a lesser number of lenses is attached may be adopted.

Figure 8A:
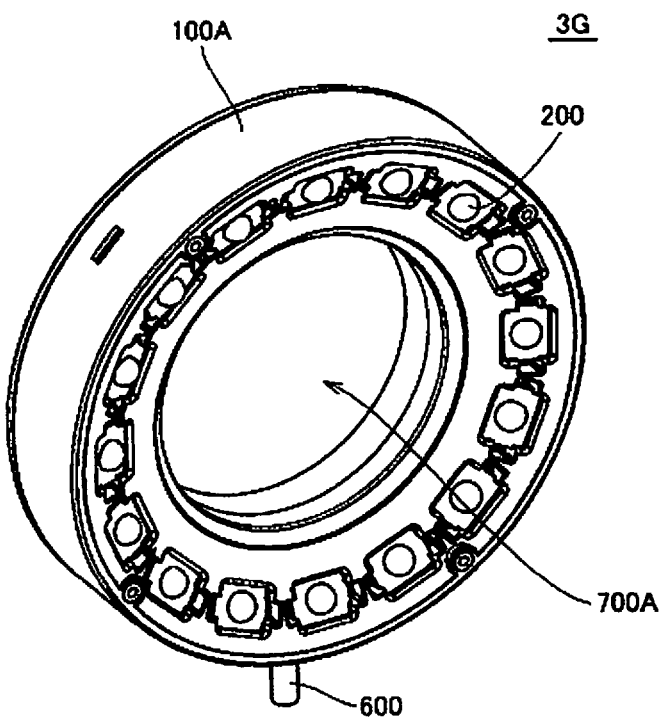
FIGS. 8A and 8B are views showing an outer appearance of the illuminating device according to the present embodiment.
Figure 8B:
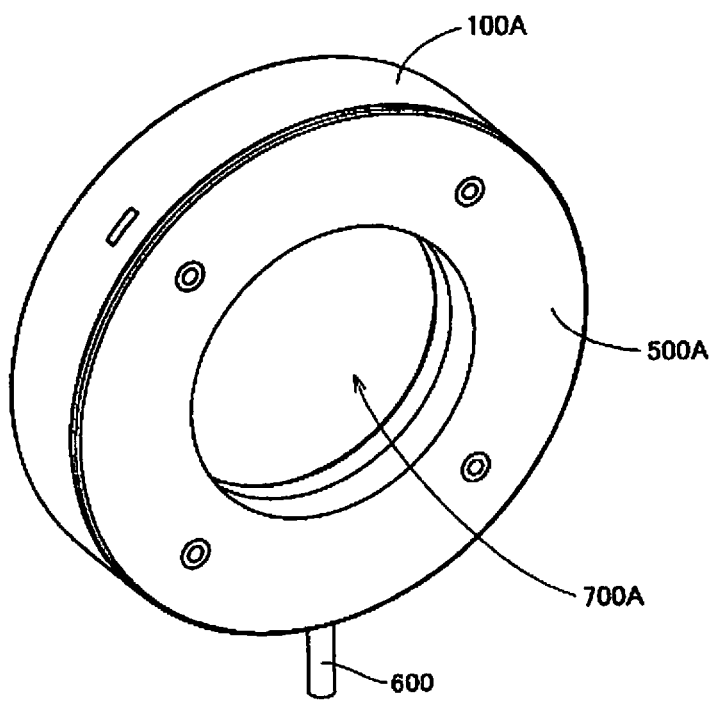
Figure 9A:
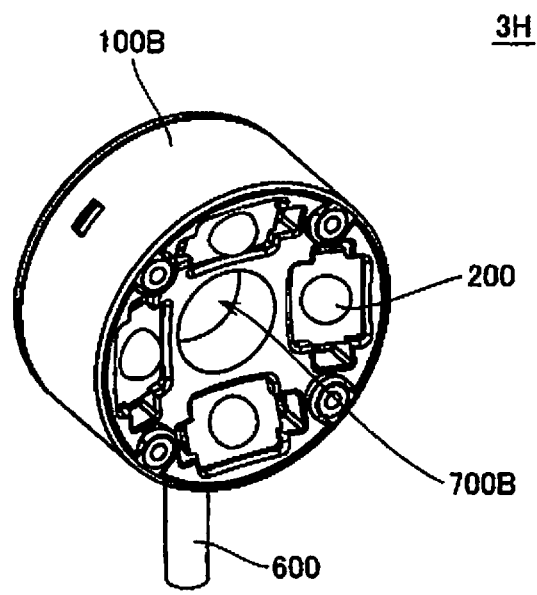
FIGS. 9A and 9B are views showing an outer appearance of the illuminating device according to the present embodiment.
Figure 9B:
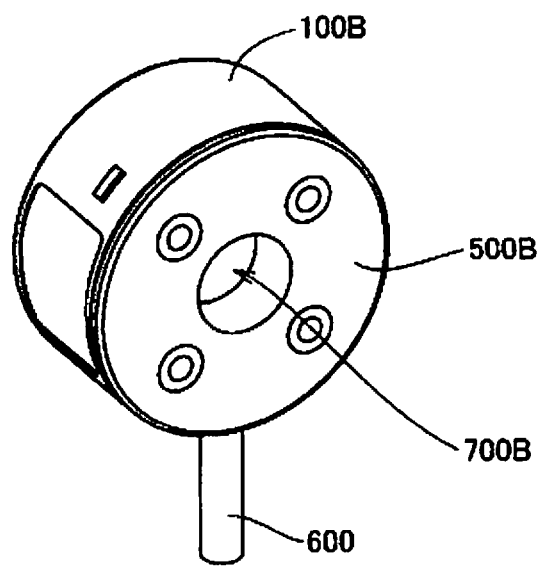

FIG. 8A and FIG. 9B show the irradiation surface side of illuminating devices 3G and 3H, respectively, and FIG. 8B and FIG. 9B show the rear surface side of the illuminating devices 3G and 3H, respectively.

As shown in FIGS. 8A and 8B, a configuration in which a greater number of lenses 200 (and light emitting elements) is attached in comparison with the illuminating device 3F shown in FIGS. 7A and 7B may be adopted. In the example shown in FIGS. 8A and 8B, the diameter of a center hole 700A is basically greater than the diameter of the center hole 700 of the illuminating device 3F shown in FIGS. 7A and 7B. However, the lenses 200 same as the lenses 200 used in the illuminating device 3F shown in FIGS. 7A and 7B may be used.

On the other hand, as shown in FIGS. 9A and 9B, a configuration in which a lesser number of lenses 200 (and light emitting elements) is attached in comparison with the illuminating device 3F shown in FIGS. 7A and 7B may be adopted. In the example shown in FIGS. 9A, and 9B, the diameter of a center hole 700B is basically smaller than the diameter of the center hole 700 of the illuminating device 3F shown in FIGS. 7A and 7B. However, the lenses 200 same as the lenses 200 used in the illuminating device 3F shown in FIGS. 7A and 7B may be used.

D. Basic Structure

The basic structure for manufacturing the illuminating device according to the present embodiment will now be described.

[d1. Basic Structure I]

Figure 10:
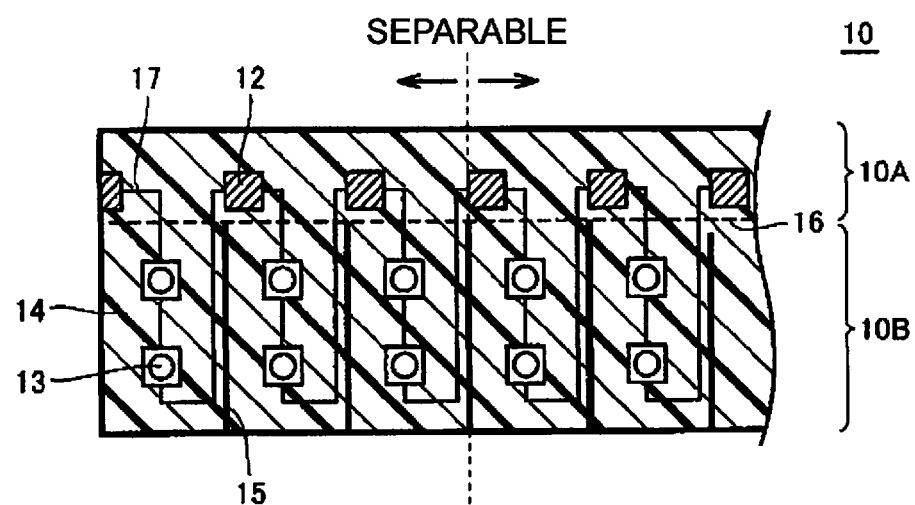
FIG. 10 is a schematic view showing a substrate for manufacturing the illuminating device according to the present embodiment.

FIG. 10 is a schematic view showing a substrate 10 for manufacturing the illuminating device according to the present embodiment. With reference to FIG. 10, the substrate 10 shown in FIG. 10 is a so-called flexible printed substrate (hereinafter also referred to as a "flexible substrate"), and is formed with light emitting elements (LED) and wiring etc. for supplying power to the light emitting elements. More specifically, substrate 10 has a conducting foil indicating the wiring pattern formed on a film-like insulator (base film), and then is covered with an insulator.

In particular, substrate 10 is formed with a bent portion 16 along the long side direction at a predetermined position in the short side direction. In other words, the substrate 10 can be divided into a common portion 10A and an individual portion 10B where the relative positional relationship there between changes by the bent portion 16. The common portion 10A and the individual portion 10B are both made of flexible substrate.

In the individual portion 10B, separating portions 15 are formed along the short side direction at every predetermined interval in the long side direction. The separating portions 15 separate the individual portion 10B to units 14 for every predetermined interval in the long side direction. In other words, it can be viewed as a plurality of reed-shaped units 14 coupled to one common portion 10A. By way of example, each of the separating portions 15 is realized by forming a perforated line (holes at a predetermined interval) on the substrate 10.

Two or more light emitting elements 13 for emitting light are mounted on each unit 14. More specifically, light emitting elements 13 are mounted on a predetermined position of the unit 14 (individual portion 10B) by surface mounting or bare chip mounting. Furthermore, the lens may be mounted in correspondence with each light emitting element 13.

The common portion 10A is a member for supplying power to light emitting elements 13 mounted on each unit 14, where an electrode extending along the long side direction is formed and conductive pads 12 are formed at every predetermined interval. As hereinafter described, when an arbitrary number of units 14 are separated as one unit, each of the pads 12 becomes the portion for supplying power to the separated substrate piece. Each pad 12 is thus arranged on or near the extended line of the corresponding separating portion 15.

Furthermore, wiring 17 connected in series with the light emitting elements 13 mounted on each individual portion 10B is formed between the common portion 10A and the individual portion 10B. In other words, with regards to each individual portion 10B, wiring 17 electrically connects the corresponding pad 12 of the common portion 10A and the first light emitting element 13, and sequentially connects the first light emitting element 13 and the adjacent light emitting element 13 in series. Wiring 17 electrically connects the last light emitting element 13 and the pad 12 corresponding to the unit 14 adjacent to its unit.

With such a wiring structure, pads 12 exist at both ends of each separated substrate piece and all light emitting elements 13 included in the relevant substrate piece can be driven by simply applying a predetermined voltage between two pads 12 regardless of along which separating portion 15 the substrate 10 is separated.

As described above, substrate 10 according to the present embodiment is made from a soft and bendable raw material. Furthermore, substrate 10 is formed with wiring that can supply power to a plurality of light emitting elements 13. The substrate can be folded between the common portion 10A and the individual portion 10B, where the individual portion 10B contains the reed-shaped units 14 on which the light emitting elements 13 can be mounted on at least one surface. In the individual portion 10B, the reed-shaped units 14 each having the same shape and structure are repeated.

As hereinafter described, the illuminating device of various modes can be manufactured by shaping the common portion 10A to a target shape. The substrate 10 is typically handled in a state of being wound around a reel, and is pulled out and cut into units of necessary length. Such a manufacturing method is adaptable to the case of continuously manufacturing the same type of illuminating device and the case of manufacturing a wide variety of illuminating devices. Substrate 10 according to the present embodiment has pad 12 arranged on the extended line of the separating portion 15 for separating the adjacent units 14, and hence the power can be supplied from both end sides of the cut common portion 10A as long as in units of multiples of the unit 14 even if the substrate is cut to any length.

[d2. Basic Structure II]

Figure 11:
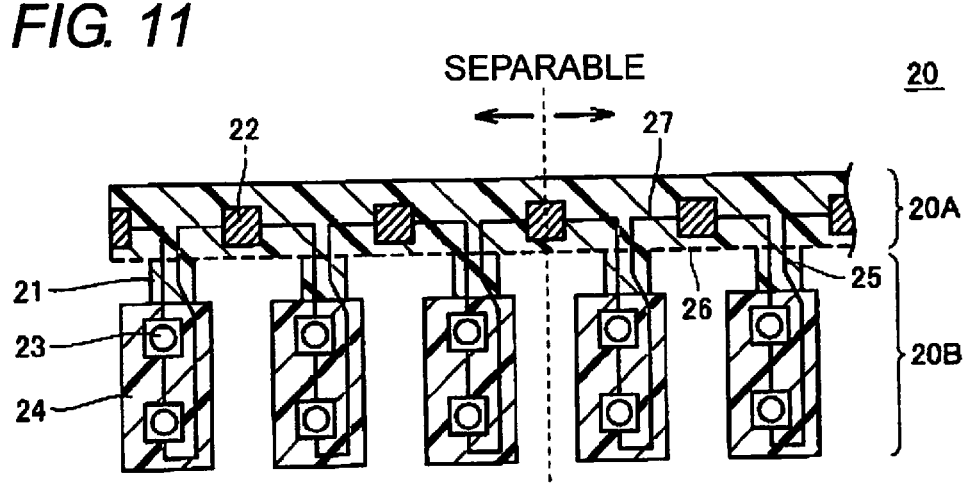
FIG. 11 is a schematic view showing a substrate of another mode for manufacturing the illuminating device according to the present embodiment.

FIG. 11 is a schematic view showing a substrate 20 of another mode for manufacturing the illuminating device according to the present embodiment. With reference to FIG. 11, substrate 20 includes a common portion 20A which is a flexible substrate, and an individual portion 20B connected to the common portion 20A. The individual portion 20B includes a plurality of units 24, where two or more light emitting elements (LED) 23 for emitting light are mounted on each unit 24. Each unit 24 is made of a material (typically, glass epoxy substrate) harder than the material of the common portion 20A. Mounting of the light emitting elements 23 to each unit 24 is thereby facilitated. Light emitting elements 23 are mounted at a predetermined position of the unit 24 (individual portion 20B) by surface mounting or bare chip mounting. Furthermore, the lens may be mounted in correspondence with each light emitting element 23.

More specifically, the common portion 20A has a planer shape as if a T-shape is continued, where the substrate configuring the unit 24 is electrically and mechanically joined to each of T-shaped portions 21.

The substrate 20 is formed with the bent portion 26 along the long side direction at each T-shaped portion 21. In other words, the relative positional relationship between the common portion 20A and the individual portion 20B can be changed with the bent portion 26 as a center.

The common portion 20A is a member for supplying power to the light emitting elements 23 mounted on each unit 24, where an electrode extending along the long side direction is formed and conductive pads 22 each are formed at substantially an intermediate position of the two adjacent T-shaped portions 21. As hereinafter described, the pad 22 becomes the portion for supplying power to the separated substrate piece when separated with an arbitrary number of units 24.

Wiring 27 connected in series with the light emitting elements 23 mounted on each individual portion 20B is formed between the common portion 20A and the individual portion 20B. Similar to wiring 17 shown in FIG. 10, wiring 27 supplies power to a plurality of light emitting elements 23.

With such a wiring structure, substrate 20 can be separated along one of the pads 22, so that all the light emitting elements 23 included in the substrate piece can be driven by simply applying a predetermined voltage between two pads 22 that exist at both ends of each separated substrate piece.

As described above, common portion 20A of substrate 20 according to the present embodiment is made from a soft and bendable raw material. Individual portion 20B of substrate 20 is made from a harder raw material that facilitates mounting of light emitting element 23. The substrate can be folded between common portion 20A and individual portion 20B, where the individual portion 20B contains reed-shaped unit 24 on which light emitting elements 23 are mounted on at least one surface. Therefore, illuminating devices of various modes can be manufactured by shaping the common portion 20A to a target shape.

Substrate 20 is typically handled in a state of being wound around a reel, and is pulled out and cut into units of necessary length. Such a manufacturing method is adaptable to the case of continuously manufacturing the same type of illuminating device and the case of manufacturing a wide variety of illuminating devices.

E. Manufacturing Process

Figure 12:
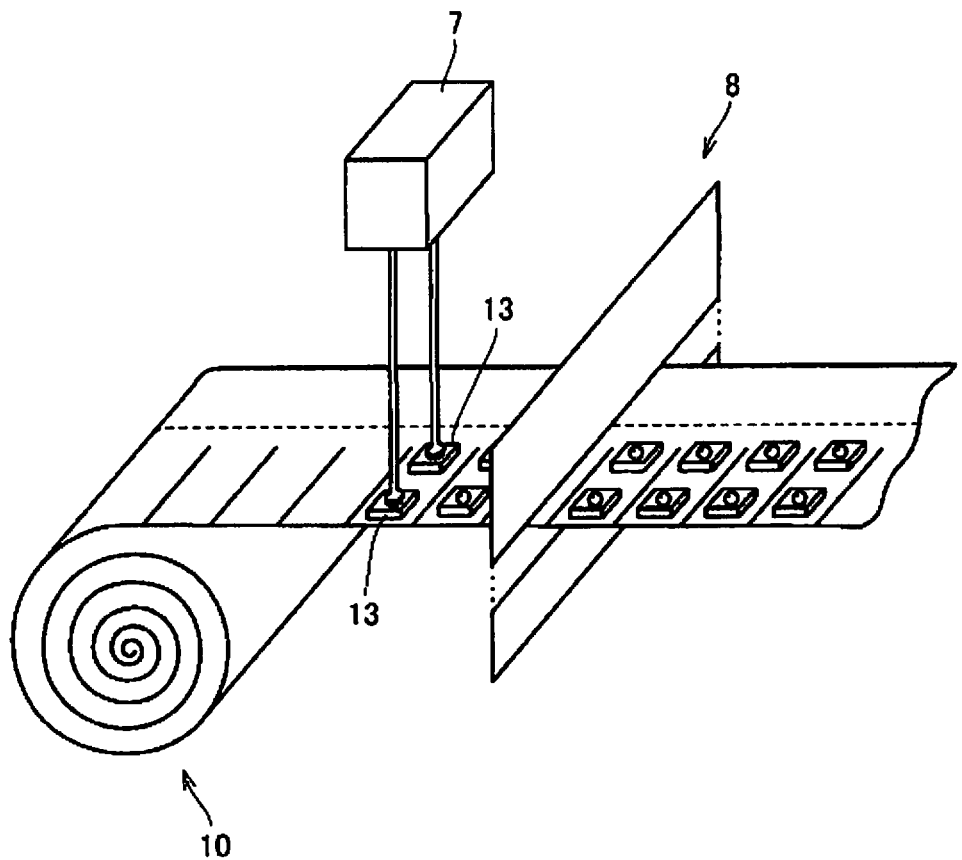
FIG. 12 is a view for describing a manufacturing process of the illuminating device according to the present embodiment.
Figure 13:
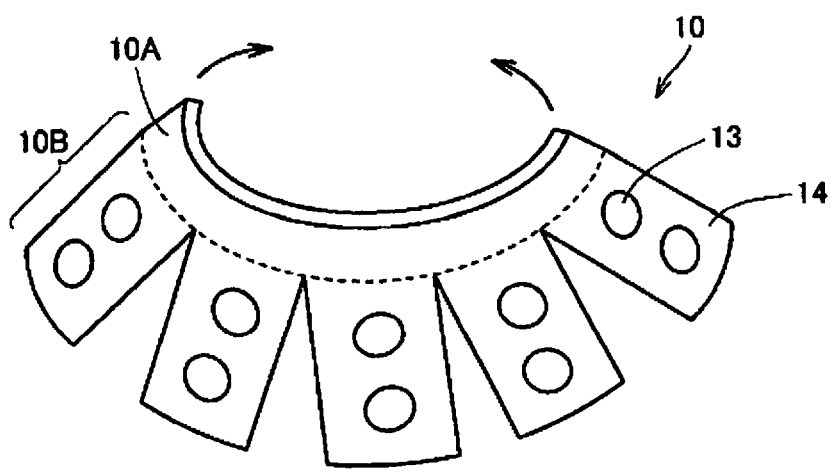
FIG. 13 is a view for describing the manufacturing process of the illuminating device according to the present embodiment.
Figure 14:
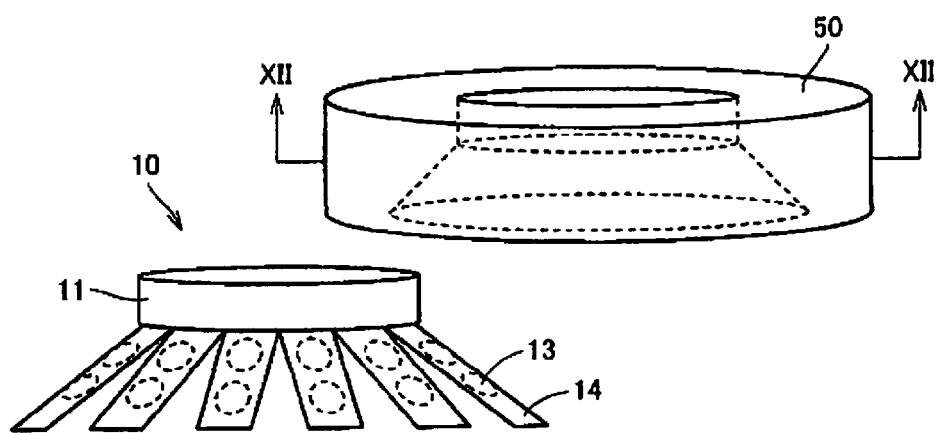
FIG. 14 is a view for describing the manufacturing process of the illuminating device according to the present embodiment.
Figure 15:
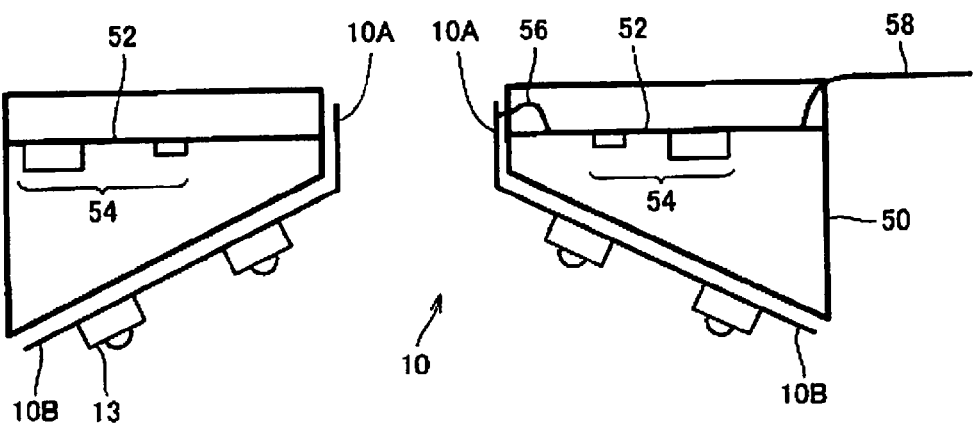
FIG. 15 is a view for describing the manufacturing process of the illuminating device according to the present embodiment.

FIG. 12 to FIG. 15 are views for describing the manufacturing process of the illuminating device according to the present embodiment. In particular, FIG. 12 shows the first process of creating a necessary substrate piece, FIG. 13 shows the second process of forming the created substrate piece, FIG. 14 shows the third process of physically connecting the formed substrate piece to the housing, and FIG. 15 shows the fourth process of electrically connecting the formed substrate piece connected to the housing. In the example shown in FIGS. 12 to 15, the process used in manufacturing the illuminating device using substrate 10 shown in FIG. 10 is shown by way of example, but similar manufacturing processes can be adopted when using substrate 20 shown in FIG. 11.

First, as shown in FIG. 12, substrate 10 in a state of being wound around a reel is sent out at a predetermined speed and the light emitting elements 13 (chip LEDs) are sequentially mounted at a predetermined position on substrate 10 using a robot 7. Substrate 10 mounted with light emitting elements 13 is then cut into units of length (necessary number of units 14), corresponding to the illuminating device to be manufactured, using a cutter 8 having a blade parallel to the short side direction of substrate 10.

In other words, in the first process, substrate 10 mounted with light emitting elements 13 is cut in the first direction (short side direction) to create the substrate piece. As described above, substrate 10 includes a first flexible portion (common portion 10A), and a plurality of second portions (individual portion 20B/unit 14) that can be bent with respect to the first portion. The first portion (common portion 10A) extends in the second direction (long side direction) orthogonal to the first direction (short side direction), and includes pads arranged at every interval defined in advance in the second direction (long side direction). Each unit 14 is connected to the first portion (common portion) between two continuous pads 12, and includes wiring 17 for electrically connecting the terminals of the mounted light emitting elements 13 and the two corresponding pads 12.

More specifically, a command is given to cutter 8 to cut at a timing that the necessary number of units 14 exist on the right side in the plane of the blade of the cutter 8 since the substrate 10 is sent out at a predetermined speed. In this case, the alignment process is performed so that one of the separating portions 15 of the substrate 10 and the position of the blade of the cutter 8 coincide with each other. More specifically, the chip LEDs are first mounted as the light emitting elements on substrate 10, and then substrate 10 is cut into an appropriate length at the position of the separating portion 15. In other words, the cutting length is changed according to the shape of the illuminating device to be manufactured.

Substrate 10 is cut in the short side direction at the position where pad 12 exists.

The cutting of substrate 10 does not necessarily need to be automated, and may be manually performed.

As shown in FIG. 13, the substrate piece of substrate 10, created by cutting, forms the common portion 10A to a shape corresponding to the illuminating device to be manufactured. In the example shown in FIG. 13, an example of forming the common portion 10A to a circular shape (ring shape) is shown, but the cross-sectional shape may be polygonal or an ellipse. The common portion 10A is typically a flexible substrate and can be easily formed to a shape corresponding to the illuminating device to be manufactured.

As shown in FIG. 14, the substrate piece of formed substrate 10 is physically connected to housing 50. Housing 50 shown in FIG. 14 is used when manufacturing the direct ring type illuminating device shown in FIG. 2 and the like, where the inner surface thereof is formed into a bowl shape and a circular void portion is formed at the center part thereof. The substrate piece of formed substrate 10 is physically joined to the inclined portion etc. of the inner surface of housing 50. In this case, the substrate piece of substrate 10 and housing 50 are fixed using a lock member such as a screw, an auxiliary member for sandwiching the substrate piece of the substrate 10 and the housing 50, and the like.

In other words, common portion 10A is fixed to the housing 50 and the relative position of the individual portion 10B (each unit 14) with respect to the common portion 10A is respectively positioned.

After the substrate piece of the substrate 10 is fixed to housing 50, the drive circuit substrate arranged inside or at a proximate position of the housing 50 and the substrate piece of the substrate 10 are electrically connected. In other words, wiring for supplying power to the pad 12 arranged in the substrate piece of the substrate 10 is formed.

FIG. 15 shows a cross-sectional view taken along line XI-XI of FIG. 14. By way of example, drive circuit substrates 52 for the light emitting elements 13 are arranged at the upper side inside the housing 50, and drive circuit substrates 52 and the pair of pads 12 in the substrate piece of the substrate 10 are electrically connected through a lead wire 56, as shown in FIG. 15. Each of the drive circuit substrates 52 is formed into a cylindrical shape, and is mounted with a drive circuit (transistor etc.) for driving the light emitting element at a predetermined position. The power is externally supplied to drive circuit substrate 52 through a lead wire 58.

As shown in FIG. 15, light emitting elements 13 are mounted on the substrate piece of the substrate 10 with the lower side in the plane of the drawing corresponding to the surface that irradiates when attached to the housing 50. An example in which the substrate piece of the substrate 10 is fixed to housing 50 while the drive circuit substrate 52 is incorporated in advance inside housing 50 is shown, but drive circuit substrate 52 may be prepared exterior to housing 50 and the power may be directly supplied from such an external drive circuit substrate 52 to the substrate piece of the substrate 10.

The illuminating device is basically manufactured through the procedures shown in FIGS. 12 to 15. Thus, the illuminating device can be manufactured by mounting the light emitting elements (chip LEDs) on each reed-shaped unit and forming only the common portion 10A in the substrate piece of the substrate 10 to the target shape. Therefore, illuminating devices having various complex shapes can be realized without imposing a mechanical stress on the mounted light emitting element (chip LED).

F. Application Example

One example of the illuminating device manufactured by the manufacturing method described above will now be described.

[f1. Direct Ring Shape]

Figure 16A:
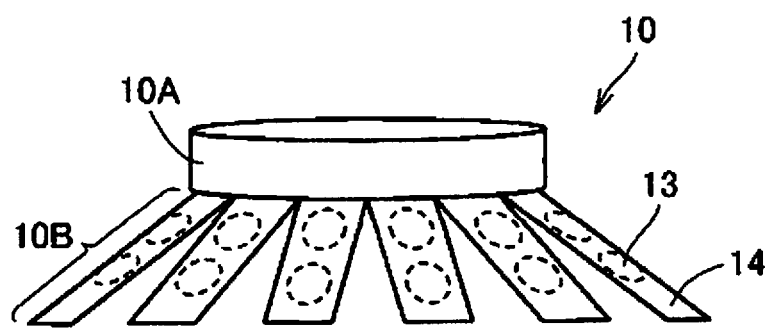
FIGS. 16A to 16C are views for describing a direct ring type illuminating device manufactured using the manufacturing method according to the present embodiment.
Figure 16B:
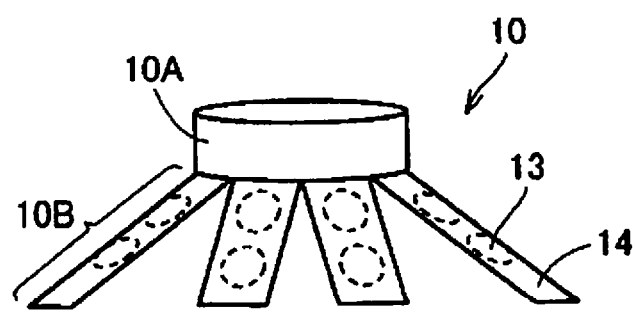
Figure 16C:
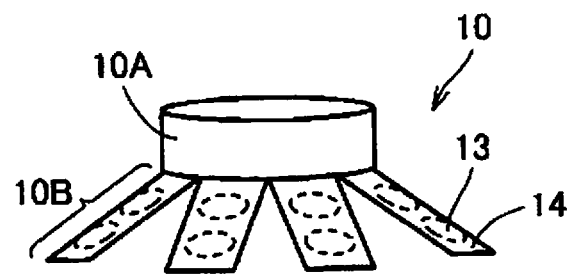

FIGS. 16A to 16C are views describing the direct ring type illuminating device manufactured using the manufacturing method according to the present embodiment. That is, FIGS. 16A to 16C show one example of a process used in manufacturing a direct ring type illuminating device 3A as shown in FIG. 2.

A large number of variations (product groups) for the illumination field and the illumination distance need to be accommodated for the direct ring type illuminating device as shown in FIG. 2 according to the field range etc. of the camera 2 to be coupled. According to the manufacturing method of the present embodiment, the size of the substrate piece to use for the illuminating device, that is, the number of units 14 to be arranged in one substrate piece can be arbitrarily set, and the shape of the common portion 10A in the substrate piece can also be an arbitrary shape.

As shown in FIGS. 16A to 16C, the number of units 14 to be arranged in the substrate piece, the shape of the common portion 10A (e.g., radius when forming to a ring shape, etc.) and the like can be freely changed according to the diameter of the void portion, the size (area) of the irradiation surface, the irradiation angle, and the like of the direct ring type illuminating device to be manufactured.

Various direct ring type illuminating devices then can be manufactured using the common substrate 10.

(f1-1: Illumination Intensity Adjustment)

Figure 17A:
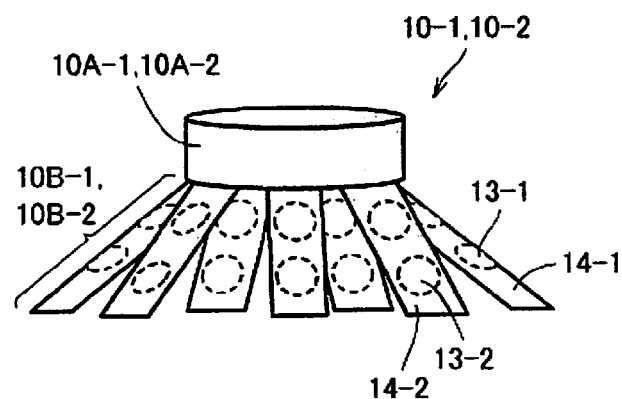
FIGS. 17A and 17B are views for describing a direct ring type illuminating device with enhanced illumination intensity manufactured using the manufacturing method according to the present embodiment.
Figure 17B:
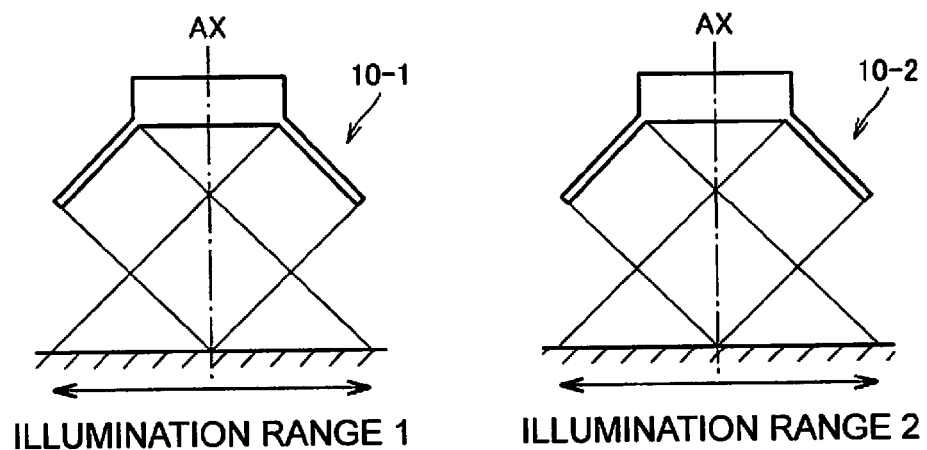

FIGS. 17A and 17B are views describing a direct ring type illuminating device with enhanced illumination intensity manufactured using the manufacturing method according to the present embodiment. In particular, FIG. 17A shows the positional relationship of two shaped substrate pieces 10-1 and 10-2, and FIG. 17B shows the illumination range of the present illuminating device.

As shown in FIG. 17A, a plurality of (two in the example of FIGS. 17A and 17B) substrate pieces 10-1 and 10-2 are formed into a similar structure, and then the two substrate pieces 10-1 and 10-2 are arranged in a shifted manner so that the irradiation positions of respective light emitting elements 13-1 and 13-2 do not overlap. With this, the illumination intensity can be enhanced compared to when one substrate piece is used. In other words, the substrate pieces 10-1 and 10-2 are arranged with the relative angle in between different on the common optical axis.

In other words, a plurality of substrate pieces are created from common substrate 10, and each of the substrate pieces is formed according to the illuminating device to be manufactured. Furthermore, the formed substrate pieces are fixed in a predefined positional relationship. As shown in FIG. 17B, substrate pieces 10-1 and 10-2 are both configured to substantially the same shape, so that the ranges (illumination ranges 1 and 2) irradiated with light from each substrate piece (light emitting element) substantially coincide. Therefore, the irradiation intensity in the common illumination range can be enhanced by fixing two substrate pieces (arraying on the same optical axis AX) to the same housing.

(f1-2: Illumination Range Adjustment)

Figure 18A:
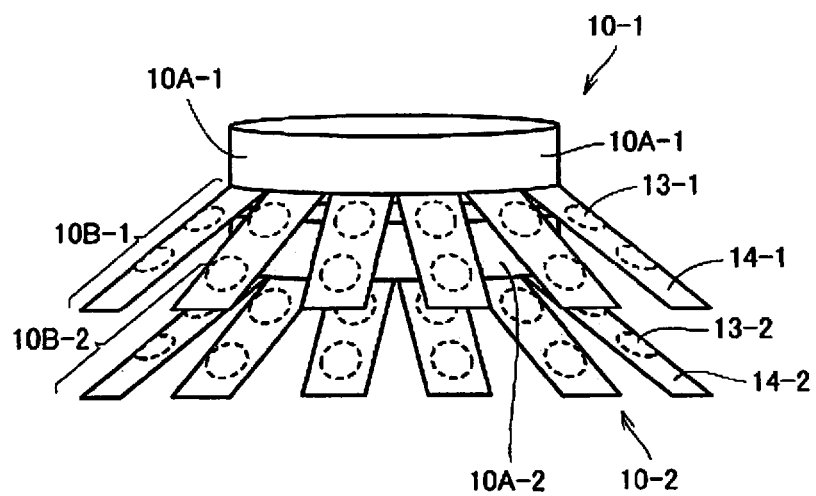
FIGS. 18A and 18B are views for describing the direct ring type illuminating device in which the illumination range is further adjusted using the manufacturing method of the present embodiment.
Figure 18B:
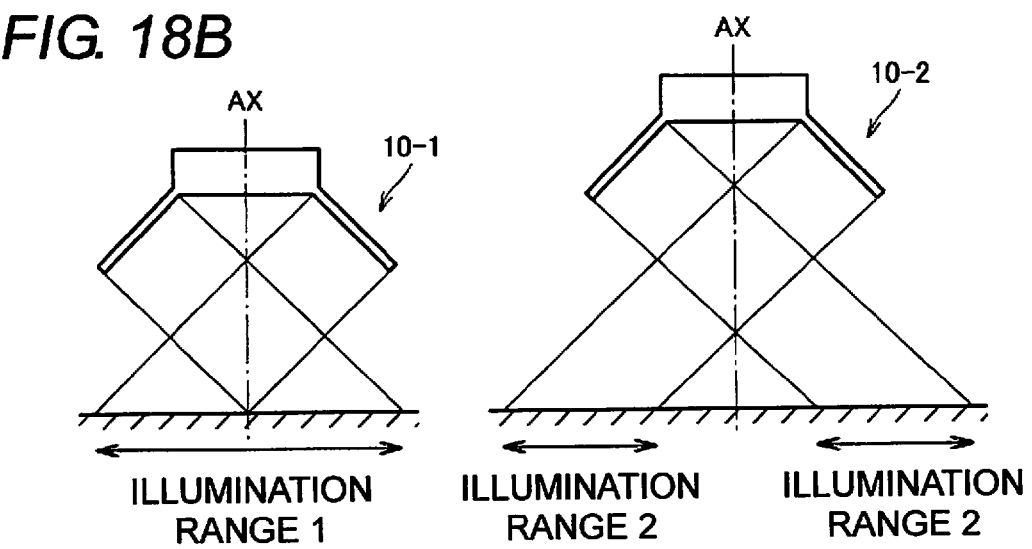

FIGS. 18A and 18B are views for describing the direct ring type illuminating device in which the illumination range is further adjusted using the manufacturing method of the present embodiment. In particular, FIG. 18A shows the positional relationship of the two shaped substrate pieces 10-1 and 10-2, and FIG. 18B shows the illumination range of the present illuminating device.

As shown in FIG. 18A, a plurality of (two in the example of FIGS. 18A and 18B) substrate pieces 10-1 and 10-2 are formed into a similar structure, and then the two substrate pieces 10-1 and 10-2 are arranged in a shifted manner in the up and down direction in the plane of the drawing so that the illumination range can be enlarged compared to when one substrate piece is used. In other words, substrate piece 10-1 and substrate piece 10-2 are arranged on the common optical axis separated by a predetermined distance.

In other words, a plurality of substrate pieces are created from the common substrate 10, and each of the substrate pieces is formed according to the illuminating device to be manufactured. Furthermore, the formed substrate pieces are fixed in a predefined positional relationship.

As shown in FIG. 18B, substrate pieces 10-1 and 10-2 are both configured to substantially the same shape, and thus the irradiation angle of the light emitted from the light emitting elements mounted on each substrate piece substantially coincide. However, the illumination range 1 illuminated by light emitting element 13-1 mounted on substrate piece 10-1 is a circular range having optical axis AX as the center whereas illumination range 2 illuminated by light emitting element 13-2 mounted on substrate piece 10-2 is a concentric (doughnut-shaped) range having the optical axis AX as the center since the distance from each substrate piece to the subject is different. Therefore, the illumination range of the illuminating device becomes a range corresponding to the sum of illumination range 1 and illumination range 2 shown in FIG. 18B by fixing two substrate pieces to the same housing. In other words, the illumination range can be enlarged compared to when one substrate piece is used.

(f1-3: Focus Mechanism)

Figure 19A:
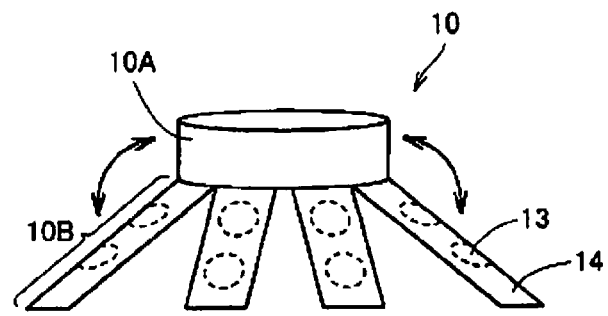
FIGS. 19A, and 19B are views for describing the direct ring type illuminating device in which the illumination range can be changed using the manufacturing method according to the present embodiment.
Figure 19B:
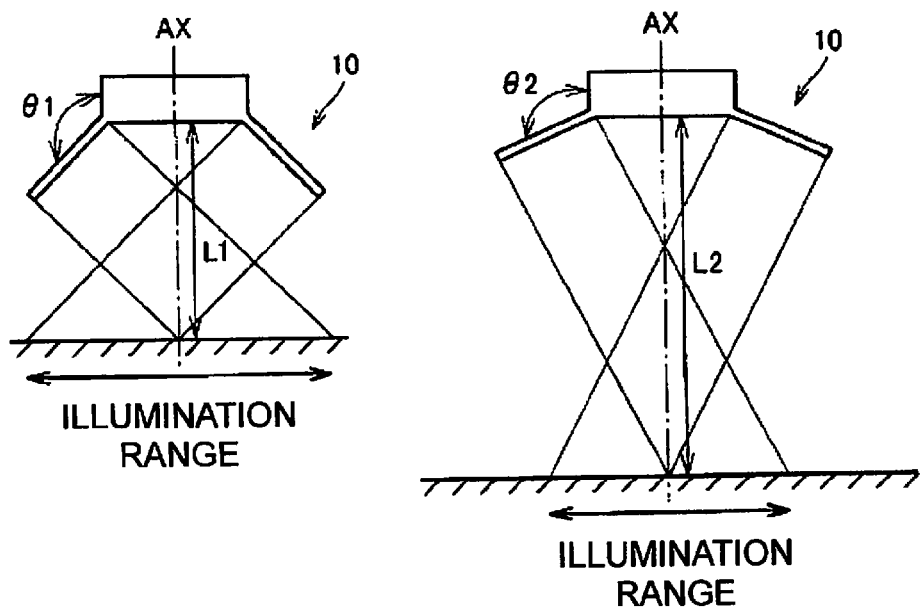

FIGS. 19A and 19B are views for describing the direct ring type illuminating device in which the illumination range can be changed using the manufacturing method according to the present embodiment. In particular, FIG. 19A shows a structure of the present illuminating device, and FIG. 19B shows the illumination range of the present illuminating device.

As shown in FIG. 19A, a mechanism (focus mechanism) for varying the relative positional relationship between common portion 10A and individual portion 10B is added with respect to the substrate piece of substrate 10 in which the common portion 10A is shaped to a ring shape. In other words, a mechanism in which the relative position of the individual portion 10B with respect to the common portion 10A can be changed is added.

Although an arbitrary structure can be adopted for such a focus mechanism, a configuration in which a housing including two members relatively movable along a common axis is prepared where one member is fixed to the common portion 10A and the other member is fixed to the individual portion 10B, so that the angel of the individual portion 10B with respect to the common portion 10A can be changed. The range in which the most appropriate illumination intensity is generated can be changed as shown in FIG. 19B by changing the angle between the common portion 10A and the individual portion 10B.

For example, when the angle between common portion 10A and individual portion 10B is θ1, the illumination range of substantially an even illumination intensity can be realized if the distance between the illuminating device and the subject is L1, and when the angle between the common portion 10A and the individual portion 10B is θ2, the illumination range of substantially an even illumination intensity can be realized if the distance between the illuminating device and the subject is L2. In other words, the distances L1, L2 are the illumination distances of the illumination device, and the illumination distance of the illuminating device can be changed in the range from L1 to L2 by changing the angle between the common portion 10A and the individual portion 10B from θ1 to θ2.

(f1-4: Evening Illumination Intensity)

Figure 20A:
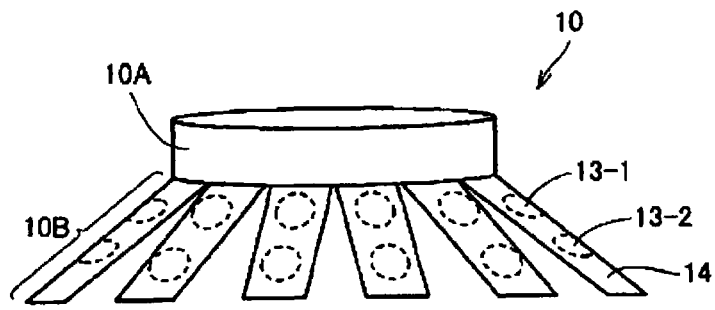
FIGS. 20A and 20B are views for describing the direct ring type illuminating device in which the illumination intensity uniformity is improved using the manufacturing method according to the present embodiment.
Figure 20B:
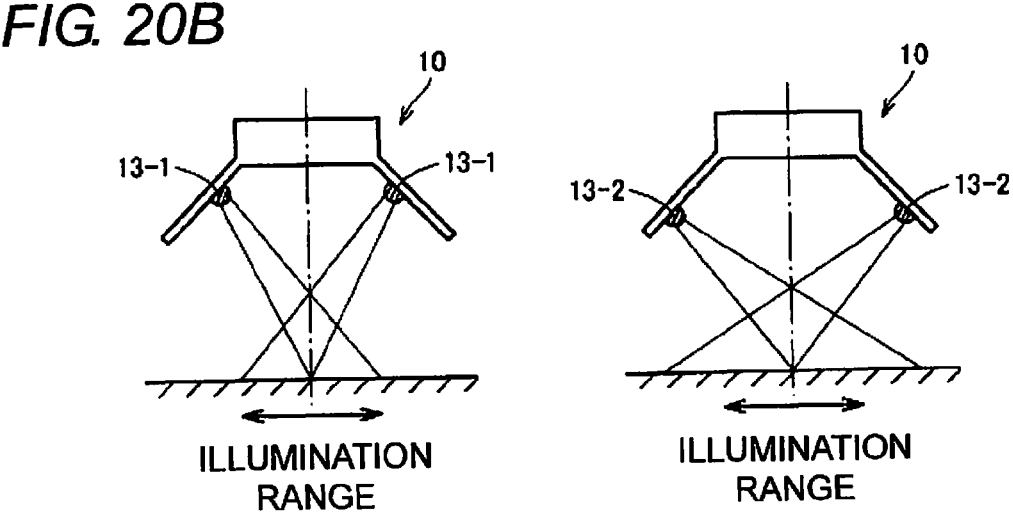

FIGS. 20A and 20B are views for describing the direct ring type illuminating device in which illumination intensity uniformity is achieved using the manufacturing method according to the present embodiment. In particular, FIG. 20A shows the structure of the present illuminating device, and FIG. 20B shows the illumination range of the present illuminating device.

In the substrate piece of substrate 10 shown in FIG. 20A, the LEDs with lenses having different irradiation fields are used for the light emitting element 13-1 mounted on the inner side and the light emitting element 13-2 mounted on the outer side.

More specifically, the LED having a relatively narrow irradiation field is used for light emitting element 13-1 on the inner side and the LED having a relatively wide irradiation field is used for light emitting element 13-2 on the outer side. Illumination intensity uniformity of the illumination range can be achieved by having the irradiation fields in such a manner.

For example, as shown in FIG. 20B, light emitting element 13-1 on the inner side illuminates a narrower range having the optical axis AX corresponding to the center axis of the substrate piece of substrate 10 as the center since the illumination field is relatively narrow, and light emitting element 13-2 on the outer side illuminates a wider range having the optical axis AX corresponding to the center axis of the substrate piece of substrate 10 as the center since the illumination field is relatively wide. Thus, the illumination intensity possibility decreases on the outer peripheral side of the illumination range by light emitting element 13-1 on the inner side, but such decrease of the illumination intensity can be compensated with the illumination light emitted from light emitting element 13-2 on the outer side. Therefore, illumination intensity uniformity in the illumination range can be achieved.

Japanese Unexamined Patent Publication No. 2002-94129, and the like are to be referenced for the light emitting element having an arbitrary illumination field as described above.

(f1-5: Countermeasures for Stray Light)

Figure 21:
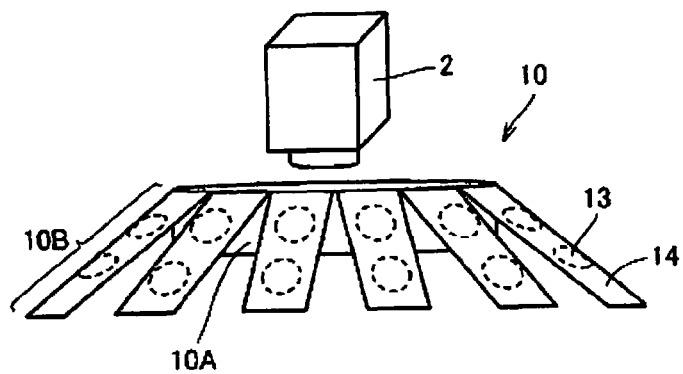
FIG. 21 is a view for describing the direct ring type illuminating device in which stray light to a camera is reduced using the manufacturing method according to the present embodiment.

FIG. 21 is a view describing the direct ring type illuminating device in which stray light to the camera is reduced using the manufacturing method according to the present embodiment.

In the example of the illuminating device described above, a configuration such that the angle of the individual portion 10B with respect to the common portion 10A is a blunt angle has been described, but the stray light to camera 2, to which the illuminating device is attached, can be reduced by configuring such that the angle of individual portion 10B with respect to common portion 10A is an acute angle. In other words, the light emitted from light emitting element 13 mounted on the individual portion 10B is suppressed from directly entering camera 2 due to the presence of common portion 10A, as shown in FIG. 21.

The appearance of the illumination light in the image data generated by the imaging of the camera 2, the occurrence of unintended halation, and the like can be avoided by suppressing such stray light.

[f2. Dome Type]

Figure 22A:
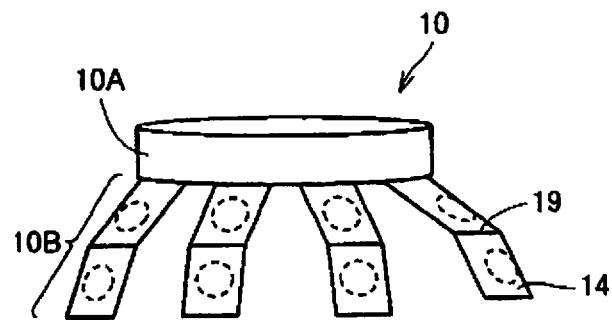
FIGS. 22A and 22B are views for describing a dome type illuminating device manufactured using the manufacturing method according to the present embodiment.
Figure 22B:
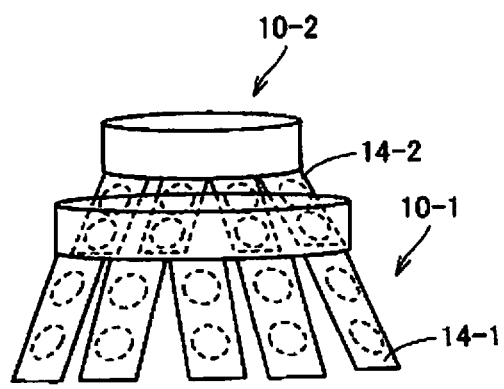

FIGS. 22A and 22B are views for describing the dome type illuminating device using the manufacturing method according to the present embodiment. In other words, FIG. 22A shows an example of a process for manufacturing the dome type illuminating device using one substrate piece, and FIG. 22B shows an example of a process for manufacturing the dome type illuminating device using a plurality of substrate pieces.

When manufacturing the dome type illuminating device as shown in FIG. 3, the irradiation surface becomes relatively wide and the curvature radius becomes relatively small.

Therefore, the irradiation surface of smaller radius can be realized by further bending each unit 14 in the structure shown in FIG. 22A, and the irradiation surface of smaller radius can be realized by stereoscopically arranging a plurality of units 14 in the structure shown in FIG. 22B.

More specifically, a bent portion 19 is formed at the portion where the light emitting element does not exist in each individual portion 10B (unit 14) connected to the common portion 10A in the illuminating device shown in FIG. 22A. The emitting direction of each light emitting element is changed by bending each unit 14 at the bent portion 19. Illumination light of uniform intensity then can be emitted from the inner surface.

The illuminating device shown in FIG. 22B is configured by substrate piece 10-1 formed so that the common portion has a certain radius, and the substrate piece 10-2 formed to have a radius smaller than the radius of the common portion of the substrate piece 10-1. Substrate piece 10-1 and substrate piece 10-2 are then stereoscopically arranged. In other words, substrate piece 10-2 is arranged so that unit 14-2 is positioned on the inner side of the center portion of substrate piece 10-1. The units 14-1 and 14-2 in which the light emitting element is mounted then can be arranged along the dome shape on the inner side by stereoscopically arranging the two substrate pieces.

[f3. Square Oblique Light Type]

Figure 23:
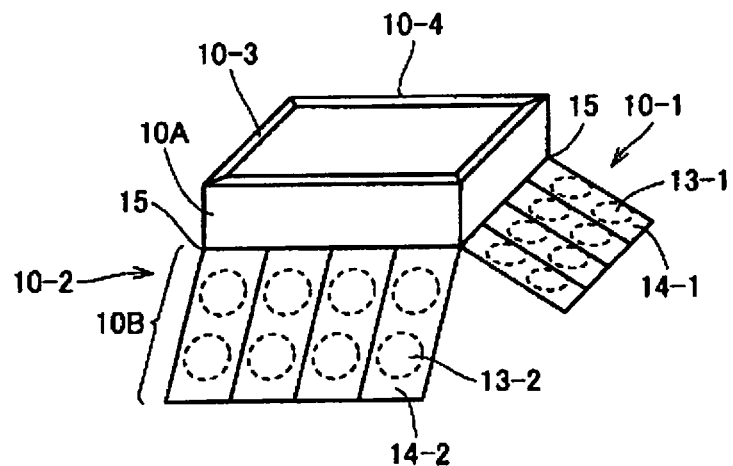
FIG. 23 is a view for describing a square oblique light type illuminating device manufactured using the manufacturing method according to the present embodiment.

FIG. 23 is a view describing a square oblique light type illuminating device manufactured using the manufacturing method according to the present embodiment.

As shown in FIG. 23, the substrate piece is prepared according to the number of directions (four directions in the example shown in FIG. 23) the illumination light is applied when manufacturing the square oblique type illuminating device (see FIG. 4). In this case, common portion 10A does not need to be formed into a circular shape as in the direct ring type described above, and a substrate piece including a predetermined number of units 14 may be prepared, the common portion of the substrate piece may be fixed to each surface of the rectangular housing, and the angle of individual portion 10B with respect to common portion 10A may be adjusted to a target value.

Therefore, when manufacturing the square oblique light type illuminating device, the number of units 14 included in each substrate piece is adjusted and the angle of individual portion 10B with respect to common portion 10A is adjusted in each substrate piece according to the size (housing size and length of irradiation surface) to realize the target specification.

Various square oblique light type illuminating devices then can be manufactured using the common substrate 10.

[f4. Bar/Line Type]

Figure 24:
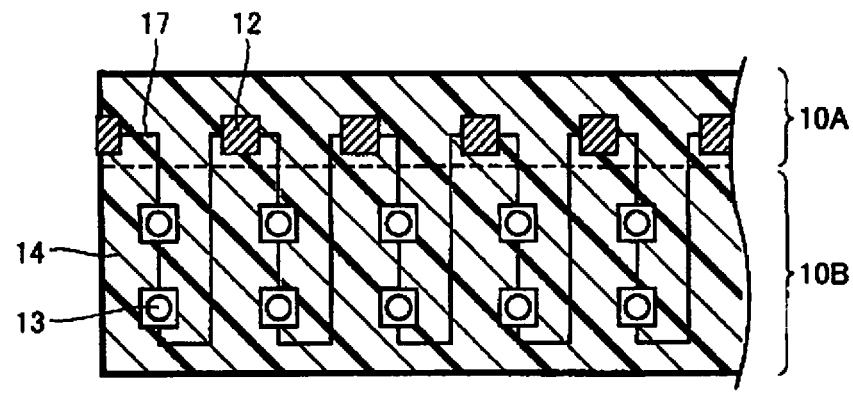
FIG. 24 is a view for describing a process for manufacturing a bar/line type illuminating device using the manufacturing method according to the present embodiment.

FIG. 24 is a view describing a process for manufacturing a bar/line type illuminating device using the manufacturing method according to the present embodiment.

As shown in FIG. 24, the substrate piece including a number of units 14 corresponding to the size of the irradiation surface is prepared when manufacturing the bar/line type illuminating device (see FIG. 5). In this case, common portion 10A does not need to be formed into a circular shape and units 14 do not need to be separated as in the direct ring type described above. As shown in FIG. 12, basically, substrate 10 in a state of being wound around a reel is merely cut into a target length and the cut substrate piece is fixed to the housing. In this case, separating portion 15 (see FIG. 10) for separating units 14 is not necessary, and hence separating portion 15 may not be formed.

Various bar/line type illuminating devices can be manufactured by adjusting the length of the cut from common substrate 10.

[f5. Directly Below Type]

Figure 25:
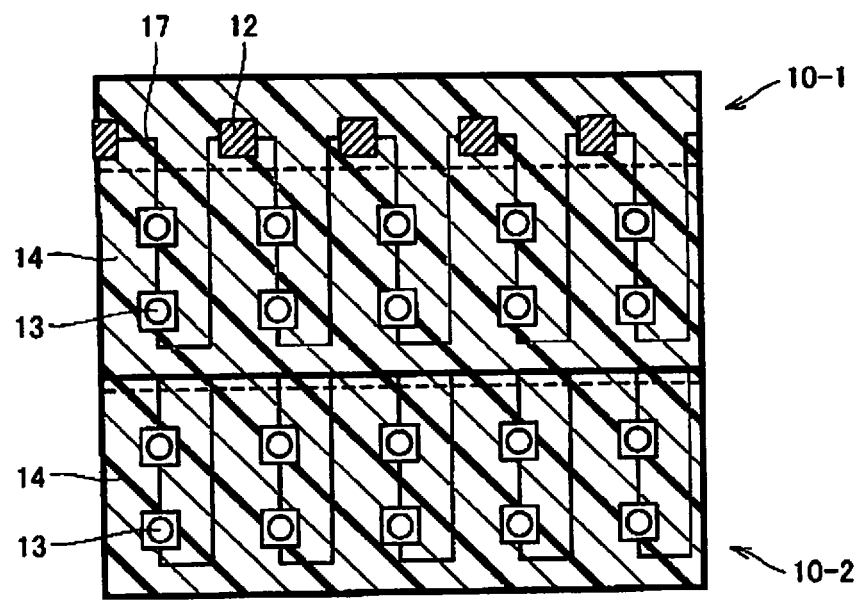
FIG. 25 is a view for describing a process for manufacturing an immediate below type illuminating device using the manufacturing method according to the present embodiment.

FIG. 25 is a view describing a process for manufacturing a directly below type illuminating device using the manufacturing method according to the present embodiment.

The directly below type illuminating device as shown in FIG. 6 needs to have the irradiation surface formed relatively large. The length in the long side direction of substrate 10 can be arbitrarily set, but the length in the short side direction of substrate 10 (range in which the light emitting elements 13 are mounted in the unit 14) may become insufficient. A sufficient irradiation area is thus ensured by arranging a plurality of substrate pieces in a line in the short side direction, as shown in FIG. 25.

In other words, when manufacturing the directly below type illuminating device, substrate pieces 10-1 and 10-2 each including a number of units 14 corresponding to the size of the irradiation surface are prepared. Substrate pieces 10-1 and 10-2 arranged in parallel are then mounted on the housing to manufacture the directly below type illuminating device. The overlapping portion of substrate piece 10-1 and substrate piece 10-2 are stereoscopically arranged. In other words, one substrate piece is arranged on the upper side and the other substrate piece is arranged on the lower side with an insulating layer and the like arranged between the substrate pieces. A wider irradiation surface can then be realized.

Various directly below type illuminating devices then can be manufactured by adjusting the length to cut from the common substrate 10.

G. Column Number Varying Structure

The structure of a substrate in which the number of columns of the light emitting elements can be changed will now be described. In other words, a substrate structure in which the length of the reed-shaped unit can be changed is illustrated.

Figure 26A:
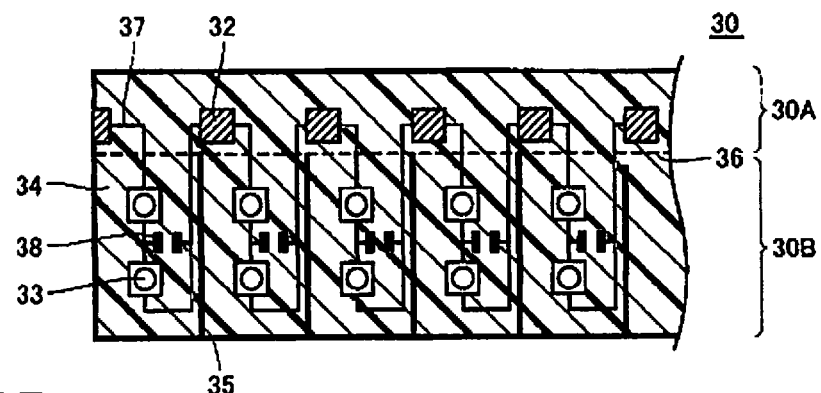
FIGS. 26A to 26D are schematic views showing a substrate of another mode for manufacturing the illuminating device according to the present embodiment.
Figure 26B:
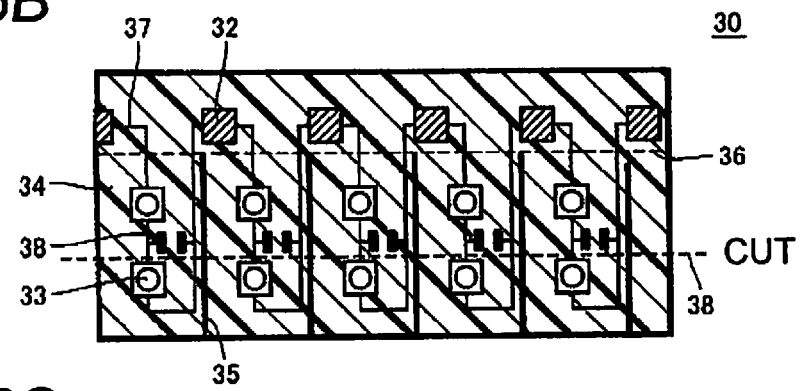
Figure 26C:
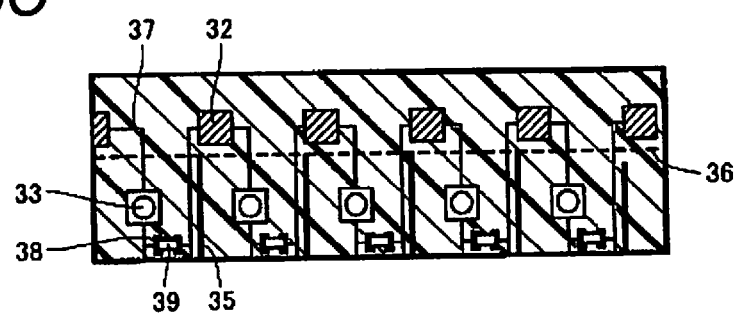
Figure 26D:
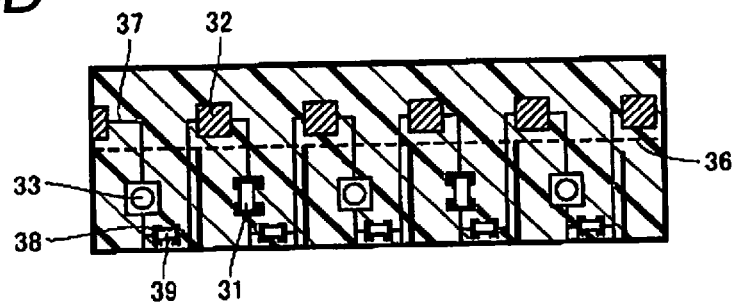

FIGS. 26A to 26D are schematic views showing a substrate of another mode for manufacturing the illuminating device according to the present embodiment. In particular, FIG. 26A shows the basic structure of the substrate 30, FIGS. 26B and 26C show a process of changing the length of the unit, and FIG. 26D shows a process of decreasing the light emitting element mounting interval.

With reference to FIG. 26A, the basic structure of substrate 30 is similar to substrate 10 shown in FIG. 10. In other words, substrate 30 includes a common portion 30A configured by a flexible substrate, and the like, and an individual portion 30B (units 34) on which the light emitting element 33 is mounted. Wiring 37 connected in series with the light emitting elements 33 mounted on each unit 34 is formed between the common portion 30A and the individual portion 30B.

In particular, by-pass terminals 38 for electrically by-passing the light emitting element positioned second in each unit 34 are formed in the substrate 30. In other words, each by-pass terminal 38 short circuits the exit side wiring of the light emitting element positioned first and the exit side wiring of the light emitting element positioned second in the corresponding unit 34. It is in an electrically non-connecting state at the time of original formation.

In other words, in the individual portion 30B (units 34), wiring 37 is formed to mount a plurality of light emitting elements 33 in series, and wiring for by-passing the light emitting element 33 positioned in the middle and the corresponding pad 32 connected in series is formed.

As shown in FIG. 26B, a case of cutting each unit 34 of the substrate 30 before the by-pass terminal 38 is considered. In other words, when manufacturing a smaller device of the direct ring type illuminating devices described above, a fewer number of light emitting elements 33 may be simply mounted on each unit 34.

Thus, the portion where light emitting elements 33 are mounted in each unit 34 is shortened as shown in FIG. 26B, and a short circuit member 39 is added to the by-pass terminal 38 of each unit 34 as shown in FIG. 26C. The power then can be supplied to the light emitting elements 33 mounted on each unit 34 through wiring 37 electrically connected to pad 32 even if the length of each unit 34 is shortened. The short circuit member 39 is a conductive member having a small resistance value that can be assumed as substantially 0Ω.

In other words, substrate 30 is cut in the first direction (short side direction), and thereafter one part of the individual portion 30B (unit 34) included in the substrate piece obtained by cutting is cut in the second direction (long side direction) and the wiring is electrically connected with the corresponding pad 32.

Furthermore, as shown in FIG. 26D, the interval at which light emitting elements 33 are mounted can be decreased by mounting the short circuit member 31 instead of mounting the light emitting element 33. In other words, in the example shown in FIG. 26D, unit 34 mounted with light emitting elements 33 is alternately provided, so that the mounting density of the light emitting element becomes substantially ½. Therefore, the pitch of the substrate piece can be substantially adjusted by mounting the short circuit member 31.

Therefore, a plurality of types of illuminating devices in which the mounting density of the light emitting element 33 is changed can be manufactured using substrate 30 shown in FIGS. 26A to 26D.

H. Configuration in which Basic Structure II is Applied to Ring Type

An example of a case where the ring type illuminating device is configured using the substrate (basic structure II) shown in FIG. 11 will be described below.

[h1. Overall Configuration]

Figure 27:
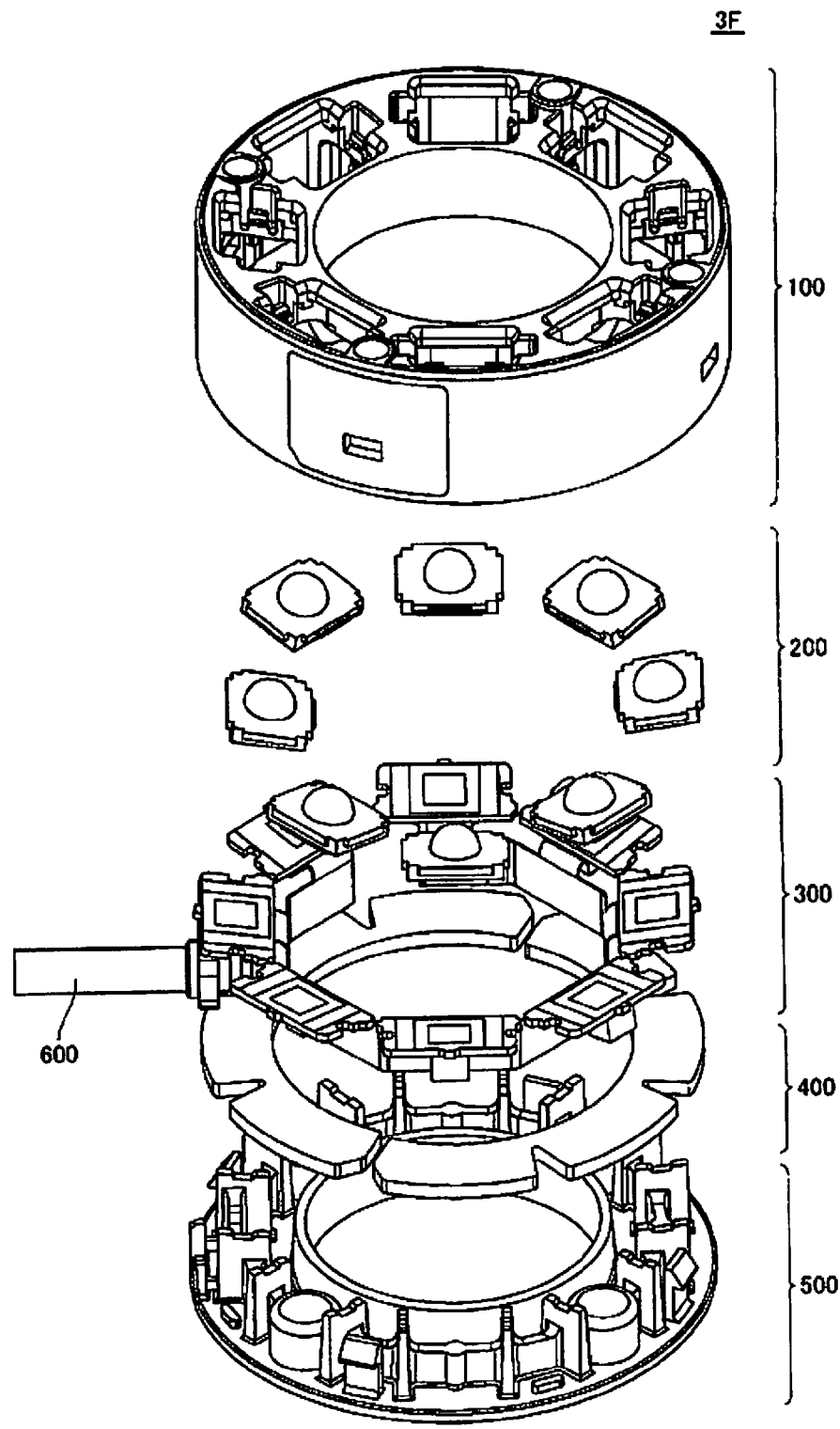
FIG. 27 is an exploded perspective view of an illuminating device according to an embodiment of the present invention.

FIG. 27 is an exploded perspective view of an illuminating device 3F according to an embodiment of the present invention.

With reference to FIG. 27, the lenses 200 are attached from the rear surface side of ring-shaped base 100 in illuminating device 3F. A window to which lenses 200 are attached in base 100 includes a holding portion for holding lenses 200 and regulating the movement of lenses 200 toward the irradiation surface (exposed surface) side of base 100.

A concentrically formed rigid flexible substrate 300 is arranged in correspondence with the arrangement form of the lenses 200. The rigid flexible substrate 300 includes a unit substrate mounted with a light emitting element corresponding to each of the plurality of lenses 200 arranged in a concentric form. The power for driving the light emitting element is supplied to the rigid flexible substrate 300 through a power supply cable 600.

A substantially circular heat dissipating sheet 400 for dissipating the heat generated in the light emitting elements of the rigid flexible substrate 300 is inserted between the rigid flexible substrate 300 and the case 500. The heat dissipating sheet 400 is made from a raw material having elasticity, and also functions as a buffer material or a pushing portion with respect to lenses 200 and rigid flexible substrate 300 inserted to a space between the base 100 and the case 500.

The case 500 is formed with projections for fixing each set including the lens 200 and the unit substrate mounted with the light emitting element at the surface on the base 100 side.

Each lens 200 is positioned so that the optical axis thereof becomes substantially perpendicular to the irradiation surface of the base 100 at the arranged position. Thus, the optical axis of each of lenses 200 is not parallel to the center axis of the center hole 700, and is held with a predetermined angle corresponding to the inclination angle of the irradiation surface. In other words, the optical axis of each lens 200 is non-parallel with respect to the center axis of the center hole 700. The respective optical axes of the lenses 200 are also non-parallel.

[h2: Basic Structure]

Figure 28A:
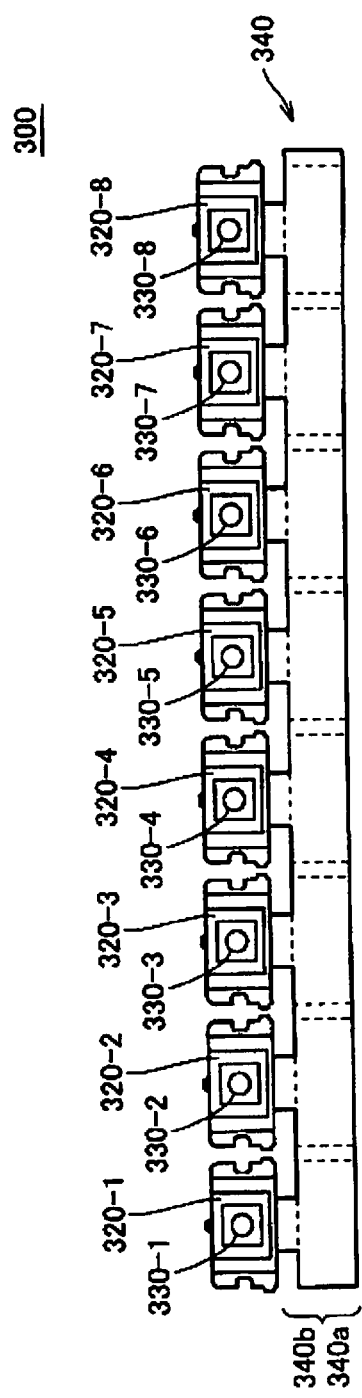
FIGS. 28A and 28B are views for describing the configuration of a rigid flexible substrate of the illuminating device according to the embodiment of the present invention.
Figure 28B:
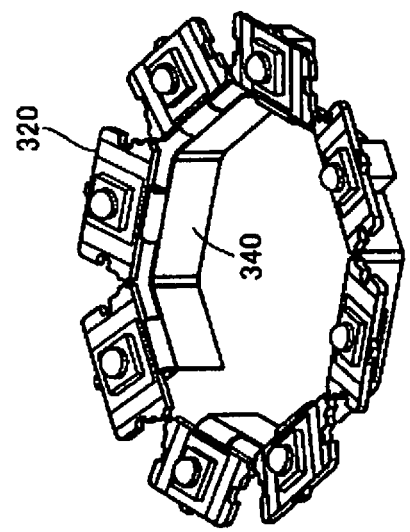

FIGS. 28A and 28B are views describing the configuration of the rigid flexible substrate 300 of the illuminating device 3F according to the embodiment of the present invention.

Figure 29:
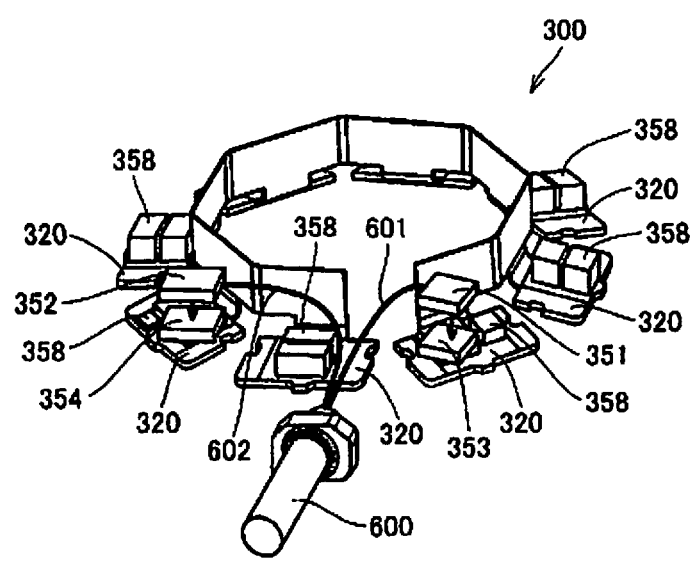
FIG. 29 is a view for describing a power supply method with respect to the rigid flexible substrate of the illuminating device according to the embodiment of the present invention.

FIG. 28A is a view showing rigid flexible substrate 300 immediate after manufacturing, and FIG. 28B is a view showing a state of rigid flexible substrate 300 before being incorporated to the base 100. FIG. 29 is a view for describing the power supply method with respect to rigid flexible substrate 300 of the illuminating device 3F according to the embodiment of the present invention.

With reference to FIG. 28A, rigid flexible substrate 300 includes a number of unit substrates 320-1 to 320-8 (also collectively referred to as "unit substrates 320") corresponding to the number of lenses 200 attached to the base 100. Each of the unit substrates 320-1 to 320-8 is configured as an object (rigid body) made from a relatively hard material for positioning and fixation described above. Specifically, unit substrates 320-1 to 320-8 are made of glass epoxy substrate.

The light emitting elements 330-1 to 330-8 (also collectively referred to as "light emitting elements 330") for emitting light are respectively mounted on the glass epoxy substrates (unit substrates 320-1 to 320-8). More specifically, each of the light emitting elements 330 is mounted at a predetermined position of each of the unit substrates 320 by surface mounting or bare chip mounting. Furthermore, a micro-lens is sometimes mounted in correspondence with each light emitting element 330. The number of light emitting elements to be mounted on each unit substrate 320 may be in plurals, and is appropriately set according to the design value (irradiation intensity) demanded on the illuminating device 3F.

The substrate does not deform even if press fitted and fixed to the base 100 and the light emitting element can be accurately positioned with respect to the lens as described above by using such a rigid substrate for unit substrate 320.

Rigid flexible substrate 300 includes a flexible printed substrate (hereinafter also referred to as a "flexible substrate") 340 for electrically connecting the unit substrates 320-1 to 320-8 (light emitting elements 330-1 to 330-8 mounted thereon). The flexible substrate 340 is formed with wiring etc. for supplying power to light emitting element 330. More specifically, flexible substrate 340 has a conducting foil indicating the wiring pattern formed on the film-form insulator (base film), and further covered with an insulator.

In other words, the illuminating device 3F incorporates unit substrates 320 which are first substrates arranged in correspondence with the plurality of lenses 200. At least one light emitting element is mounted on each unit substrate 320. Furthermore, illuminating device 3F incorporates flexible substrate 340 for electrically connecting the unit substrates 320 which are the first substrates. The unit substrate 320 is configured as a rigid body, and flexible substrate 340 is configured to have flexibility.

As shown in FIG. 28B, such a rigid flexible substrate 300 is incorporated in the base 100 after being concentrically formed as shown in FIG. 28B. In other words, in the flexible substrate 340 of the rigid flexible substrate 300, a portion 340a linearly formed over a plurality of unit substrates 320, and a portion 340b branched from the portion 340a to the respective unit substrates 320 are integrally configured. Flexible substrate 340 is folded at the portion (see FIG. 28A) indicated with a broken line of the linearly formed portion 340a, so that flexible substrate 340 is shaped to a tortoise shell shape as shown in FIG. 28B. Furthermore, flexible substrate 340 is folded to the outer peripheral side at the portion (see FIG. 28A) indicated with a broken line of the portion 340b branched to unit substrate 320, so that unit substrates 320-1 to 320-8 are formed to have a predetermined angle with respect to a plane defined by a substantially circular shape (tortoise shell shape) configured by the flexible substrate 340. When bending flexible substrate 340, a polygonal shape shown in FIG. 28B is preferable in relation to the unit substrate 320. In this case, the portion indicated with a wavy line of FIG. 28A is preferably processed to facilitate the folding. The flexible substrate 340 may be bent to a circular shape. In such a case, it may not necessarily be folded at the portion indicated with a broken line in FIG. 28A.

The unit substrate 320 does not deform even if flexible substrate 340 is bent as shown in FIG. 28B by using the rigid substrate for the unit substrate 320. Therefore, stress does not apply on the light emitting element 330 surface mounted on unit substrate 320, and reliability does not decrease.

In rigid flexible substrate 300, a predetermined planar shape is formed along the circumferential direction of the base 100 for flexible substrate 340, and each unit substrate 320 is bent at an angle corresponding to the tilt of lens 200 held in a holding portion 110 of the base 100 with respect to the corresponding portion of flexible substrate 340 (portion 340a linearly formed over a plurality of unit substrates 320). In other words, flexible substrate 340 is bent along the line of a plurality of windows 102-1 to 102-8.

As will be described later, in flexible substrate 340, the wiring pattern is formed such that light emitting elements 330-1 to 330-8 mounted on unit substrates 320-1 to 320-8 are connected in series. Thus, the power is supplied between two points on the wiring path formed by flexible substrate 340 including the light emitting element 330, so that a group of light emitting elements 330-1 to 330-8 can be lighting driven.

More specifically, as shown in FIG. 29, connectors 353 and 354 are mounted on the two unit substrates 320 positioned near the power supply cable 600 (power supply cable passing recess 150) that passes through the base 100 and the case 500 to be introduced inside of the unit substrates 320 configuring the rigid flexible substrate 300, and connectors 351 and 352 attached to the end of wirings 601 and 602 of a positive electrode and a negative electrode of the power supply cable 600 are connected to the connectors 353 and 354.

The connectors 353 and 354 are arranged in a non-parallel direction in both the longitudinal direction and the short direction of unit substrate 320. In other words, the direction of wirings 601 and 602 are connected with respect to the connectors 353 and 354 set to face the direction of the power supply cable 600 to facilitate the pulling of the wirings 601 and 602 from the power supply cable 600. In other words, flexible substrate 340 includes a pair of connectors 353 and 354 for electrically connecting with power supply cable 600 and the pair of connectors 353 and 354 arranged in the direction corresponding to the introducing position of the power supply cable 600.

As will be described later, a configuration in which a predetermined number of light emitting elements 330 connected in series is connected in parallel by the necessary number may be adopted if the number of light emitting elements 330 to be lighted is in great number.

A circuit component 358 for driving light emitting element 330 is mounted on the surface on the side not mounted with the light emitting element 330 in each unit substrate 320. In other words, in each unit substrate 320, the circuit components other than the light emitting element 330 are basically mounted on the surface on the side opposite to the surface mounted with the light emitting element 330. The space efficiency thus improves, and the substrate size of each unit substrate 320 can be reduced.

[h3: Facilitating Assembly]

As described with reference to FIG. 27, rigid flexible substrate 300 is concentrically formed, and is then inserted between base 100 corresponding to a first housing and case 500 corresponding to a second housing. At the time of assembly to the case, flexible substrate 340 in the bent state may deform and bite into base 100 corresponding to the first housing and the case 500 corresponding to the second housing. In other words, the flexible substrate 340 may interfere with the base 100 or the case 500 by collapsing to the inner side or the outer side from the original position.

Figure 30A:
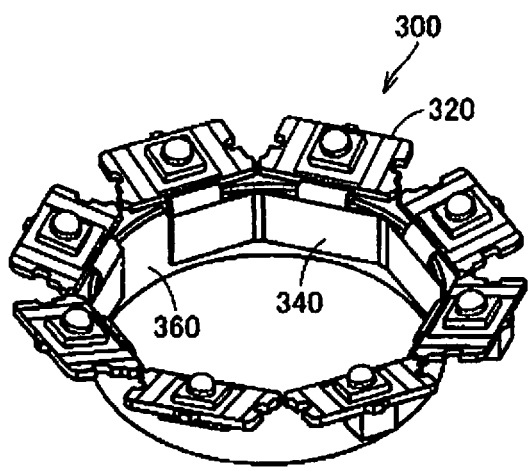
FIGS. 30A and 30B are views for describing an auxiliary fixing member attached to the rigid flexible substrate of the illuminating device according to the embodiment of the present invention.
Figure 30B:
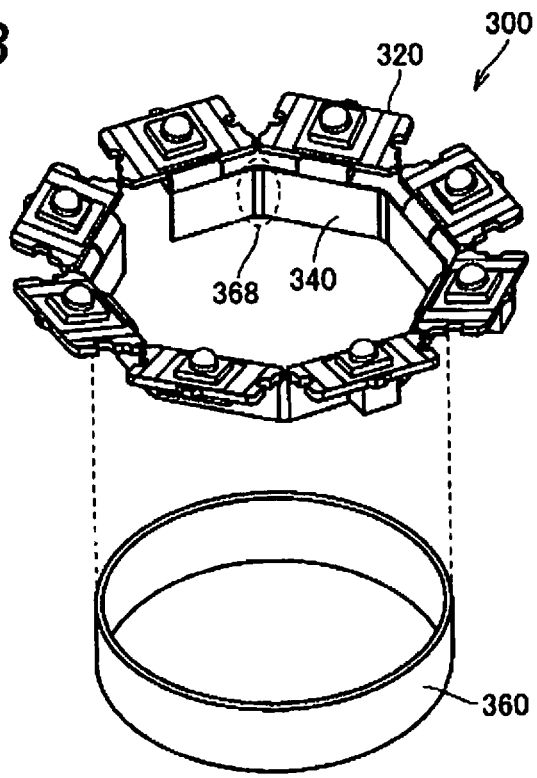

Therefore, assembly performance can be improved by using the auxiliary fixing member as shown in FIGS. 30A and 30B.

FIGS. 30A and 30B are views describing the auxiliary fixing member attached to the rigid flexible substrate of the illuminating device according to the embodiment of the present invention. FIG. 30A shows a state in which ring-shaped member 360, which is the auxiliary fixing member, is attached with respect to the concentrically formed rigid flexible substrate 300, and FIG. 30B shows a state of attaching ring-shaped member 360, which is the auxiliary fixing member, with respect to the concentrically formed rigid flexible substrate 300.

As shown in FIG. 30B, ring-shaped member 360 is used for the auxiliary fixing member. The inner diameter of the ring-shaped member is designed to be greater than the circumscribed circle of the concentrically formed flexible substrate 340 by a predetermined margin. The ring-shaped member 360 is attached to the outer peripheral side of the concentrically formed flexible substrate 340. The ring-shaped member 360 is preferably formed with a material such as resin.

Therefore, the deformation (collapsing to the inner side or the outer side from the original position) of flexible substrate 340 can be prevented by supporting flexible substrate 340 with ring-shaped member 360. An event in which flexible substrate 340 bites between base 100 corresponding to the first housing and case 500 corresponding to the second housing thus can be avoided. Assembly performance can be improved as a result.

[h4: Wiring Pattern]

An example of the wiring pattern in the rigid flexible substrate will be described below.

Figure 31:
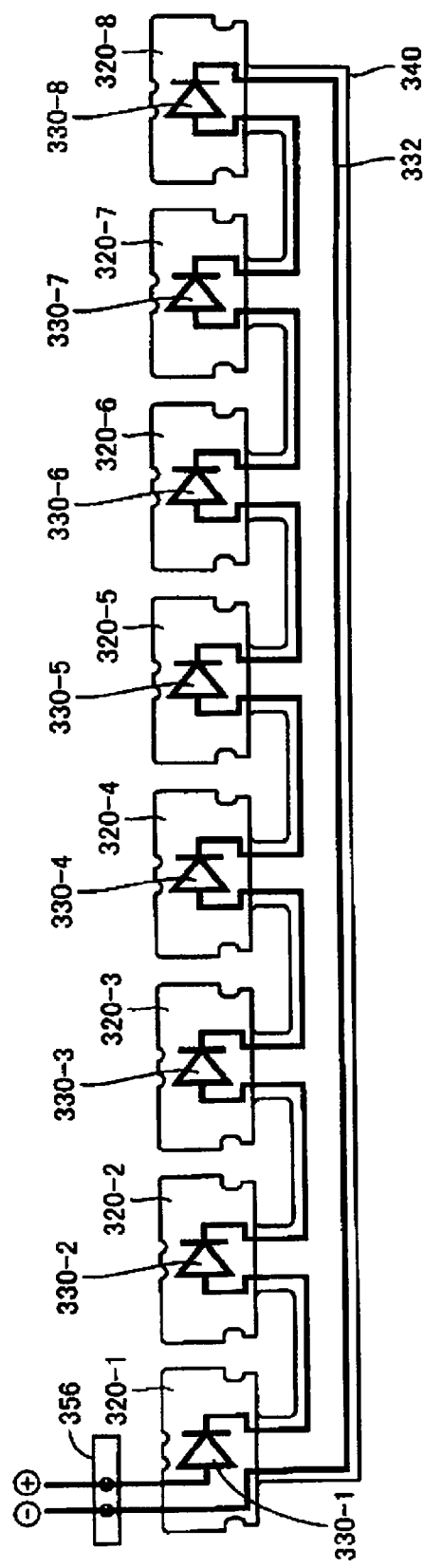
FIG. 31 is a view for describing an example of a wiring pattern in the rigid flexible substrate of the illuminating device according to the embodiment of the present invention.
Figure 32A:
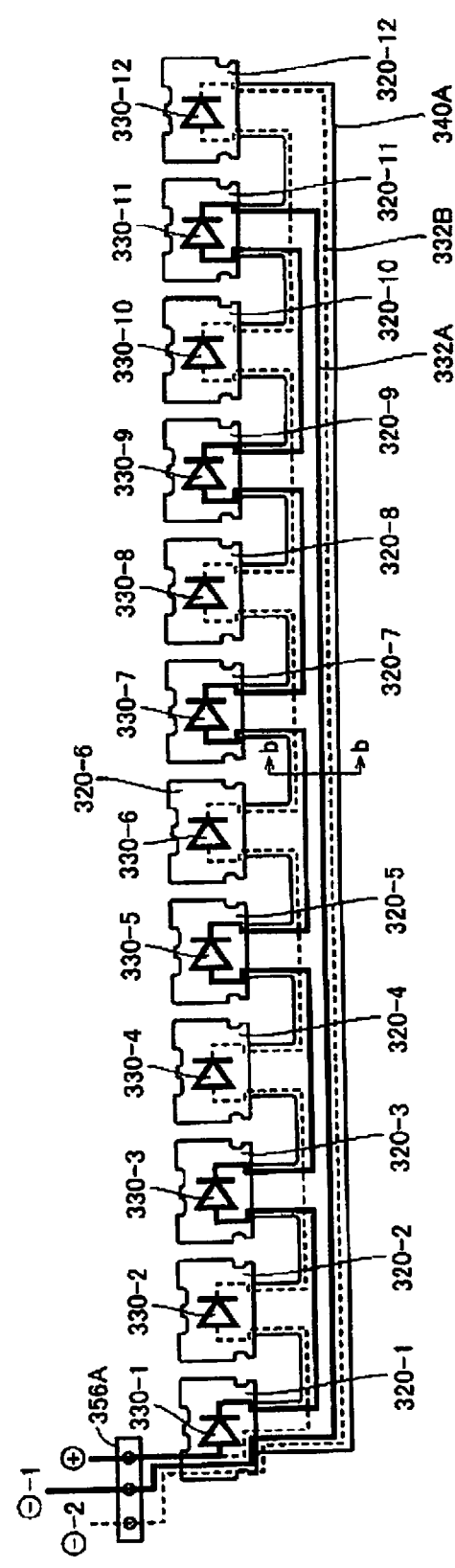
FIG. 32 is a view for describing an example of a wiring pattern in the rigid flexible substrate of the illuminating device according to the embodiment of the present invention.

FIG. 31 and FIG. 32 are views describing the example of the wiring pattern in the rigid flexible substrate of the illuminating device according to the embodiment of the present invention. FIG. 31 shows an example in which eight light emitting elements 330 are mounted on one rigid flexible substrate, and FIG. 32 shows an example in which twelve light emitting elements 330 are mounted on one rigid flexible substrate. In particular, FIG. 31 and FIG. 32 show configuration examples in which the connectors related to power supply can be concentrated to one.

In the rigid flexible substrate 330 shown in FIG. 31, a supply line 332 for connecting light emitting elements 330-1 to 330-8 respectively mounted on unit substrates 320-1 to 320-8 in series is formed on flexible substrate 340. Both ends of supply line 332 are connected to connector 356. Furthermore, they are connected to a controller for lighting the light emitting element 330, as will be described later, through the connector 356. In other words, positive potential is supplied to one end of the supply line 332 through the connector 356, and negative potential is supplied to the other end of supply line 332 through the connector 356.

In rigid flexible substrate 300A shown in FIG. 32, the twelve light emitting elements 330 are supplied with power in parallel six at a time using two supply lines 332A and 332B so that the voltage to apply to the supply line does not become excessively high. In other words, the supply line 332A shown with a solid line in FIG. 32 is formed to connect the odd numbered unit substrates 320-1, 320-3, 320-5, 320-7, 320-9, 320-11 in series, and the supply line 332B shown with a broken line in FIG. 32 is formed to pass through the even numbered unit substrates 320-2, 320-4, 320-6, 320-8, 320-10, 320-12 in series.

As hereinafter described, control is performed so that a constant current having a predetermined magnitude is supplied to the light emitting element 330, and hence the supply current of the respective supply lines 332A and 332B are controlled independent from each other so that the magnitude of the current flowing through the supply line does not vary. Thus, the respective ends of the supply lines 333A and 333B are commonly supplied with the positive potential through connector 356A, and the respective other ends of the supply lines 333A and 333B are connected to the different terminals of the negative potential through the connector 356A.

Figure 32B:
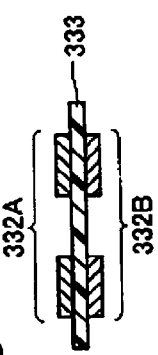

Since supply line 332A and supply line 3328 cannot intersect while maintaining insulation on flexible substrate 340, supply line 332A is generally formed on one surface of flexible substrate 340, and supply line 332B is formed on the other surface of flexible substrate 340. This example is shown in FIG. 32B.

[h5: First Variant]

The configuration shown in FIG. 33 to FIG. 36 may be adopted for the configuration of the rigid flexible substrate instead of the modes shown in FIG. 28A to FIG. 32B.

Figure 33:
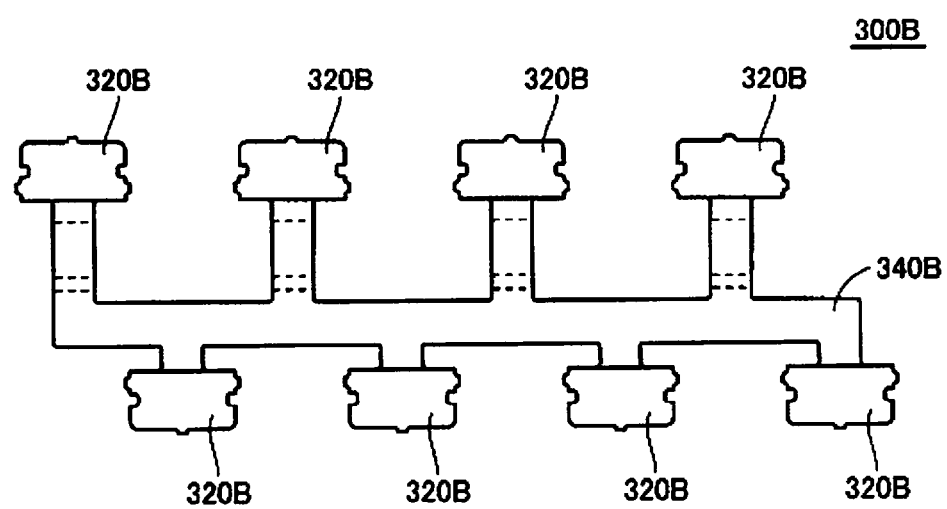
FIG. 33 is a view showing a variant of the rigid flexible substrate of the illuminating device according to the embodiment of the present invention.
Figure 34A:
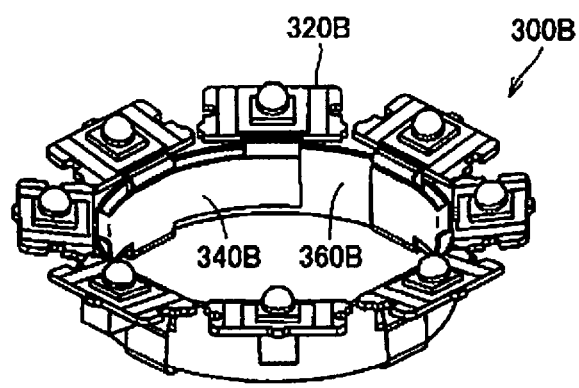
FIGS. 34A and 34B are views for describing an auxiliary fixing member attached in the variant of the rigid flexible substrate of the illuminating device according to the embodiment of the present invention.
Figure 34B:
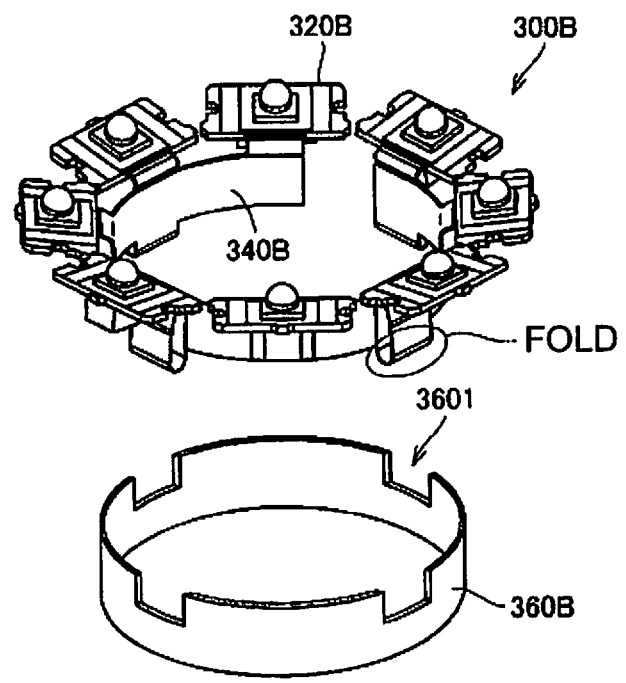
Figure 35:
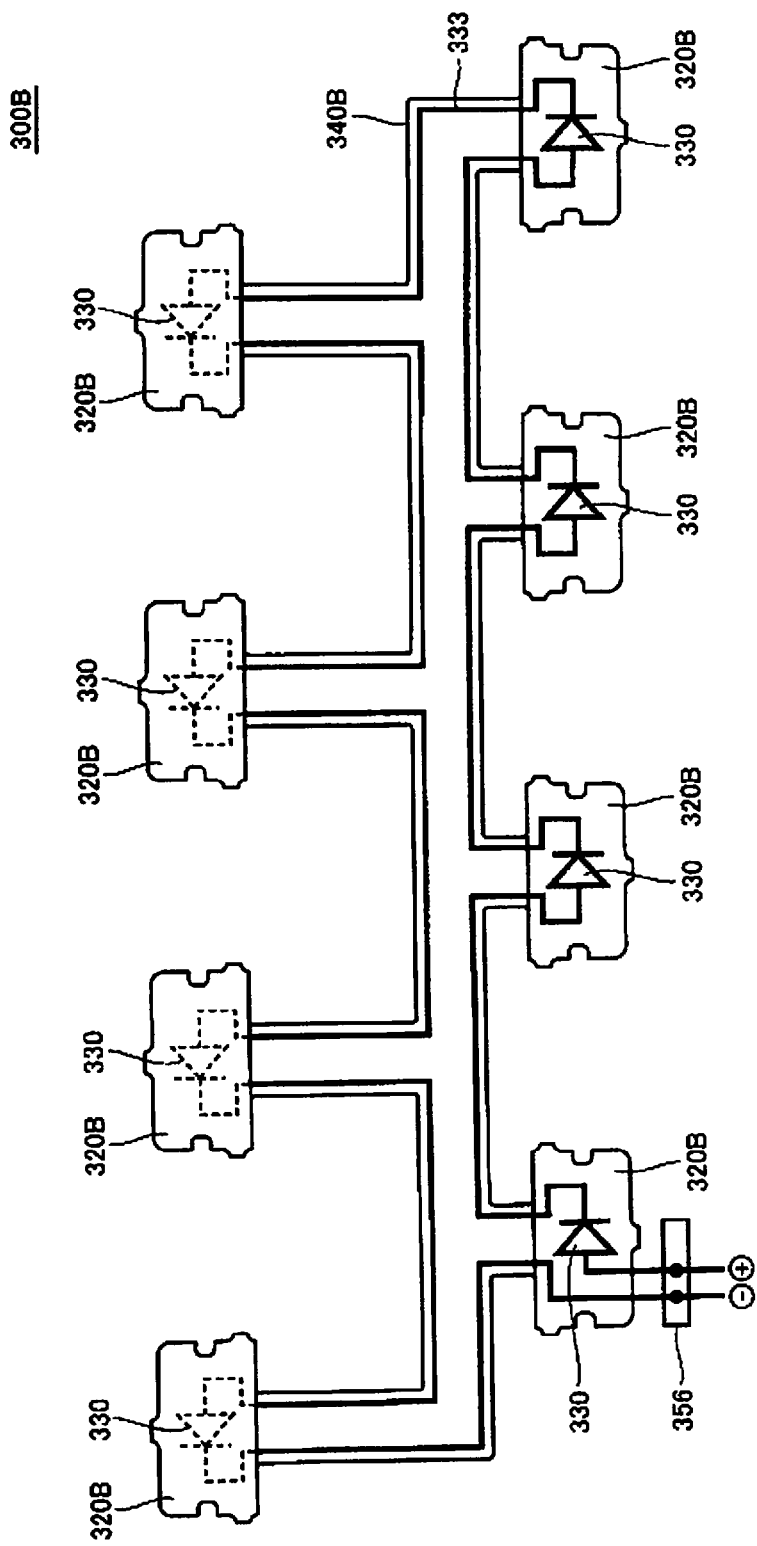
FIG. 35 is a view for describing an example of a wiring pattern in the variant of the rigid flexible substrate of the illuminating device according to the embodiment of the present invention.
Figure 36:
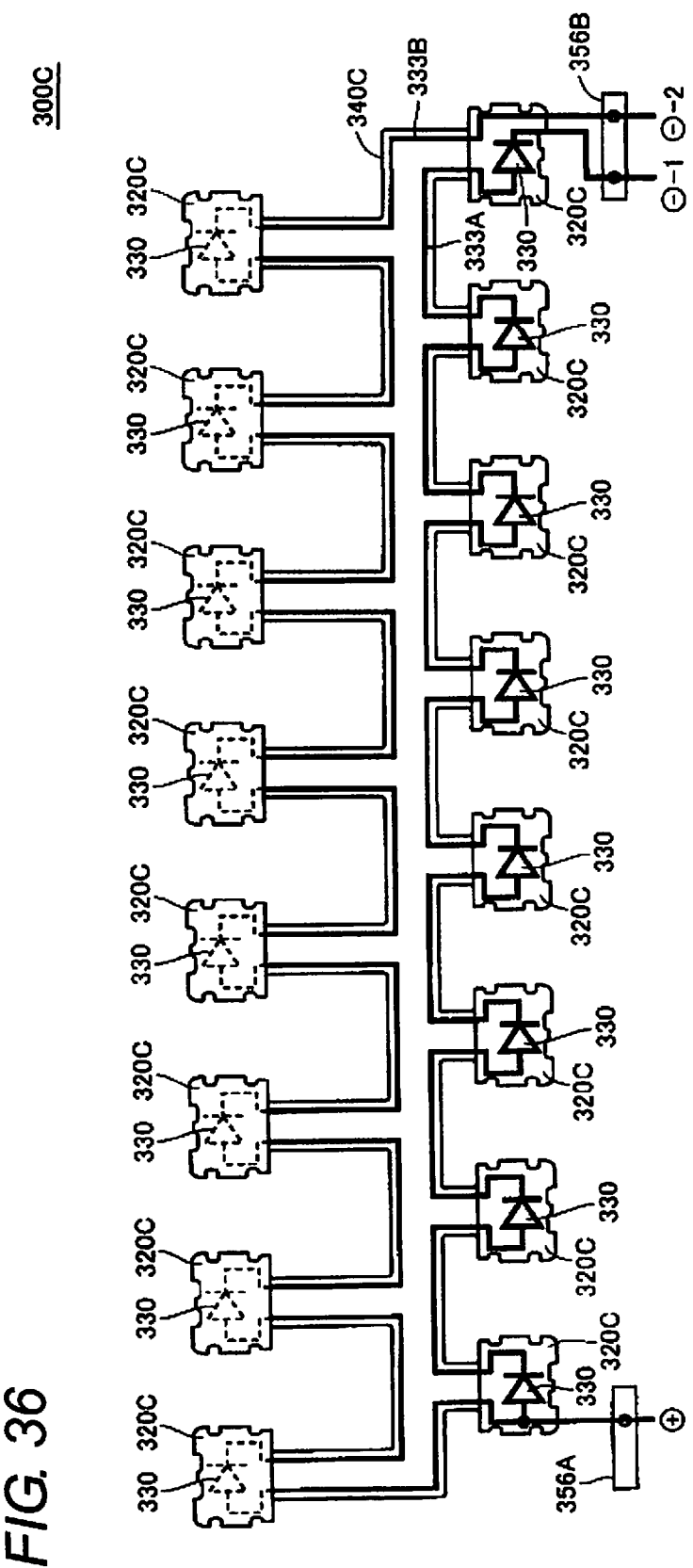
FIG. 36 is a view for describing an example of a wiring pattern in the variant of the rigid flexible substrate of the illuminating device according to the embodiment of the present invention.

FIG. 33 is a view showing a variant of the rigid flexible substrate of illuminating device 3F according to the embodiment of the present invention. FIGS. 34A and 34B are views describing the auxiliary fixing member to be attached in the variant of the rigid flexible substrate of illuminating device 3F according to the embodiment of the present invention. FIG. 35 and FIG. 36 are views describing an example of the wiring pattern in the variant of the rigid flexible substrate of the illuminating device according to the embodiment of the present invention.

With reference to FIG. 33, rigid flexible substrate 300B has a configuration in which unit substrate 320A, on which light emitting element 330 is to be mounted, is arranged in a zigzag manner (alternate arrangement on both sides). Unit substrates 320B are connected through flexible substrate 340B. Flexible substrates 300B can be configured to a shape suited for incorporation to the base 100 as shown in FIG. 29 by appropriately folding flexible substrate 340B.

More specifically, the portion of flexible substrate 340B connected with unit substrates 320B arranged on the upper side in the plane of the drawing is long compared to the portion of flexible substrate 340B connected with unit substrates 320B arranged on the lower side in the plane of the drawing. Unit substrates 320B arranged on the upper side in the plane of the drawing are folded along the up and down direction in the plane of the drawing to realize a structure similar to rigid flexible substrate 300 shown in FIG. 28A. In other words, the four unit substrates 320B arranged on the upper side in the plane of the drawing are folded at the position indicated with a broken line, and flexible substrate 340B is bent to a substantially circular shape (tortoise shell shape). Therefore, in flexible substrate 340B, the surface on which light emitting element 330 is mounted on each of the unit substrates 320B positioned on the lower side in the plane of the drawing and the surface on which light emitting element 330 is mounted on each of the unit substrates 320B positioned on the upper side in the plane of the drawing become opposite.

In other words, as shown in FIGS. 34A and 34B, the four unit substrates 320B (positioned on the upper side in the plane of drawing in FIG. 33) of rigid flexible substrate 300B are folded to the outer peripheral side, and then formed into a ring shape. In this variant as well, the auxiliary fixing member as shown in FIG. 34B is preferably used to improve the assembly performance. The ring-shaped member 360B which is the auxiliary fixing member shown in FIG. 34B is basically similar to the ring-shaped member 360 shown in FIG. 30B, but cutouts 3601 are formed at the positions corresponding to the four rigid flexible substrates 300B folded to the outer peripheral side. The cutout 3601 is the portion for absorbing the thickness that forms when the flexible substrate 340B is folded back.

Finally, as shown in FIG. 34A, the ring-shaped member 360B which is the auxiliary fixing member is attached to the concentrically formed rigid flexible substrate 300B, and then incorporated in the case.

The pitch of the unit substrate can be reduced by using the configuration described above compared to the configuration (one side arrangement) in which the unit substrate is arranged on one side in the longitudinal direction of flexible substrate 340 as shown in FIGS. 28A and 28B, and thus the ring diameter of the ultimately formed illuminating device 3F can be reduced. The rigid flexible substrate itself can be miniaturized.

With reference to FIG. 35 and FIG. 36, an example of the wiring pattern in the rigid flexible substrate 300B will be described. FIG. 35 shows an example in which eight light emitting elements 330 are mounted on one rigid flexible substrate, and FIG. 36 shows an example in which sixteen light emitting elements 330 are mounted on one rigid flexible substrate.

In rigid flexible substrate 300B shown in FIG. 35, a supply line 333 for connecting the eight light emitting elements 330 respectively mounted on the eight unit substrates 320B in series is formed on flexible substrate 340B. Both ends of supply line 333 are connected to connector 356. Furthermore, they are connected to a controller for lighting the light emitting element 330, as will be described later, through connector 356. In other words, positive potential is supplied to one end of supply line 333 through connector 356, and negative potential is supplied to the other end of supply line 333 through connector 356.

In rigid flexible substrate 300C shown in FIG. 36, the sixteen light emitting elements 330 are supplied with power in parallel eight at a time using two supply lines 333A and 333B so that the voltage to apply to the supply line does not become excessively high. In other words, supply line 333A is formed to connect unit substrates 320C arranged on the lower side in the plane of the drawing in series, and supply line 332B is formed to connect unit substrate 320C arranged on the upper side in the plane of the drawing in series.

As hereinafter described, control is performed so that a constant current having a predetermined magnitude is supplied to light emitting element 330, and hence the supply current of the respective supply lines 333A and 333B are controlled independent from each other so that the magnitude of the current flowing through the supply line does not vary. Thus, the respective one ends of the supply lines 332A and 332B are commonly supplied with the positive potential through connector 356A, and the respective other ends of supply lines 332A and 332B are connected to the different terminals of the negative potential through connector 356B.

Since supply line 333A and supply line 333B are formed so as not to intersect in the rigid flexible substrate 300C shown in FIG. 36, two supply lines 333A and 333B can be formed on one surface of the flexible substrate 340.

[h6: Second Variant]

Figure 37:
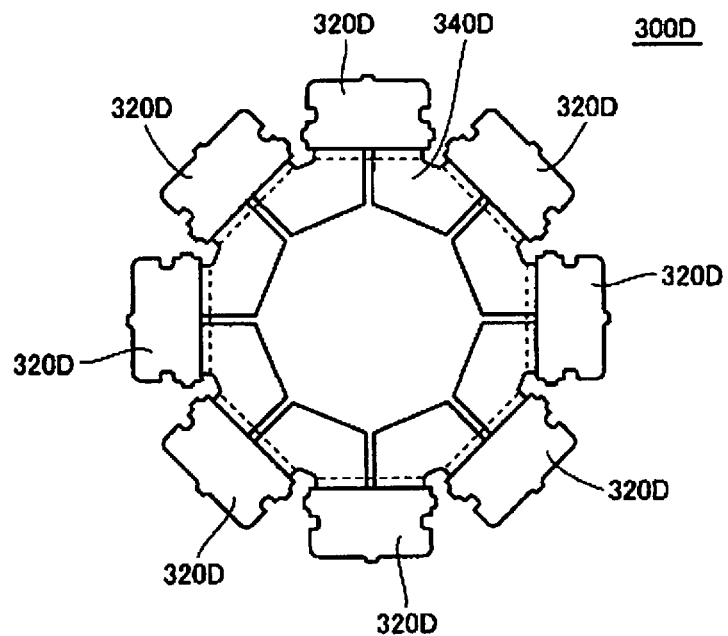
FIG. 37 is a view showing a variant of the rigid flexible substrate of the illuminating device according to the embodiment of the present invention.

FIG. 37 is a view showing a variant of the rigid flexible substrate of the illuminating device according to the embodiment of the present invention. With reference to FIG. 37, the rigid flexible substrate 300 has a configuration in which unit substrates 320D on which the light emitting element is mounted are concentrically (radially) arranged. In rigid flexible substrate 300D shown in FIG. 37, flexible substrates 340D are positioned on the center side, and unit substrates 320D are positioned on the outer peripheral side of flexible substrates 340D. Each unit substrate 320D is electrically connected with unit substrate 320D positioned adjacent thereto on both sides through flexible substrate 340D. The rigid flexible substrate 300D can be formed into a shape suited for incorporating to the base 100 as shown in FIG. 29 by appropriately folding flexible substrate 340D.

[h7: Third Variant]

Figure 38:
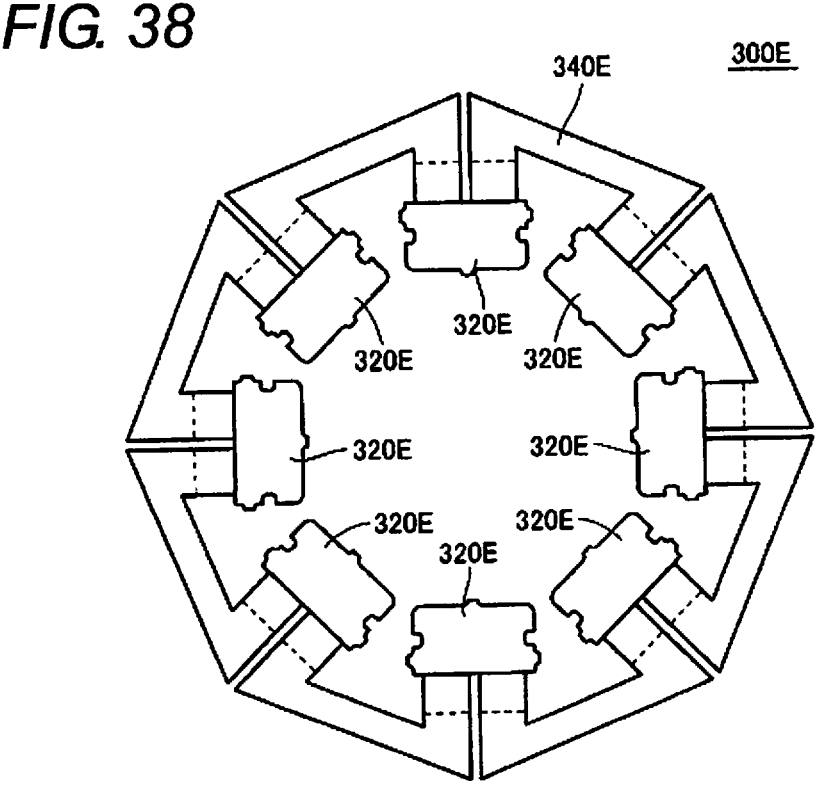
FIG. 38 is a view showing a variant of the rigid flexible substrate of the illuminating device according to the embodiment of the present invention.

FIG. 38 is a view showing a variant of the rigid flexible substrate of the illuminating device according to the embodiment of the present invention. With reference to FIG. 38, rigid flexible substrate 300E has a configuration in which unit substrates 320E on which the light emitting element is mounted are concentrically (radially) arranged, similar to the rigid flexible substrate 300D shown in FIG. 37. However, flexible substrates 340E are positioned on the outer peripheral side and unit substrates 320E are positioned on the inner peripheral side of flexible substrates 340E in rigid flexible substrate 300E shown in FIG. 38.

Each unit substrate 320E is electrically connected with unit substrate 320E positioned adjacent thereto on both sides through flexible substrate 340E. Rigid flexible substrate 300E can be formed into a shape suited for incorporating to the base 100 as shown in FIG. 29 by appropriately folding flexible substrate 340E.

[h8: Fourth Variant]

Figure 39:
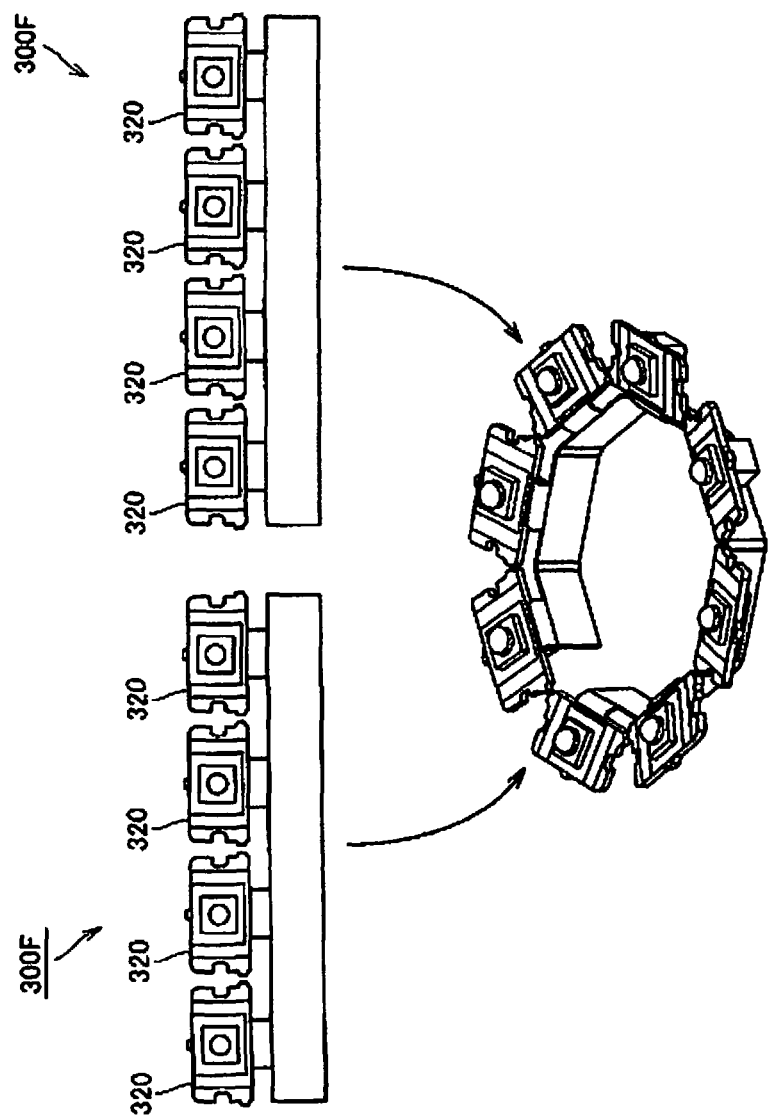
FIG. 39 is a view showing a variant of the rigid flexible substrate of the illuminating device according to the embodiment of the present invention.

FIG. 39 is a view showing a variant of the rigid flexible substrate of the illuminating device according to the embodiment of the present invention. With reference to FIG. 39, the light emitting elements may be concentrically formed into a ring shape by combining a plurality of rigid flexible substrates 300F. For example, as shown in FIG. 39, rigid flexible substrate 300F including four unit substrates 320 may be bent to configure one part (for semicircle) of the substantially circular shape (tortoise shell shape), and two of such may be combined to configure an illumination module in which the light emitting elements are configured to a ring shape.

Therefore, the type of rigid flexible substrate can be reduced even when accommodating a large number of variations (product groups) by adopting a method of combining a plurality of rigid flexible substrates including fewer number of unit substrates 320.

[h9: Embodiment of the Light Emitting Element]

In the illuminating device according to the present embodiment, light emitting element 330 is mounted on unit substrate 320. Light emitting element 330 is typically a chip LED. The embodiment described below is preferably adopted to suppress degradation caused by heat etc. generated from the chip LED itself when mounting the chip LED.

Figure 40A:
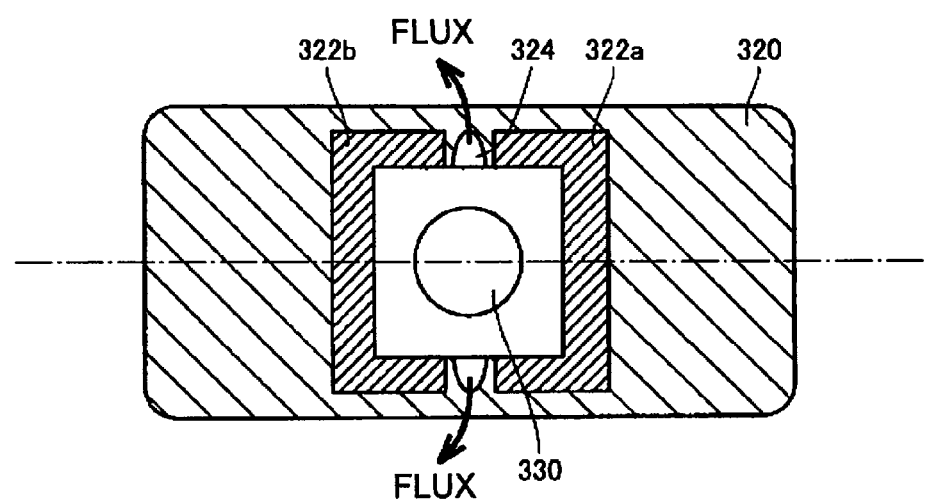
FIGS. 40A and 40B are views for describing amounting example of the light emitting element of the illuminating device according to the embodiment of the present invention.
Figure 40B:
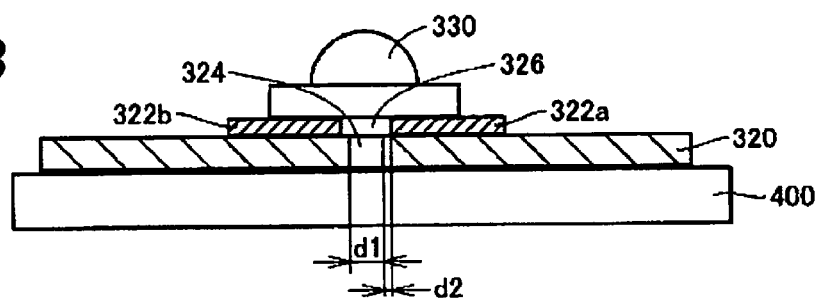

FIGS. 40A and 40B are views for describing a mounting example of the light emitting element of the illuminating device according to the embodiment of the present invention. With reference to FIGS. 40A and 40B, light emitting element 330 is arranged on lands 322a and 322b formed on unit substrate 320. The lands 322a and 322b correspond to electrodes (pads) for supplying positive potential and negative potential, respectively.

The lands 322a and 322b are arranged spaced apart by a predetermined distance. Furthermore, in illuminating device 3F according to the present embodiment, a hole 324 for discharging flux is formed in a region corresponding to the void between the lands 322a and 322b on unit substrate 320. Flux is the component contained in the solder used to mount light emitting element 330 on lands 322a and 322b. It is difficult to completely remove in the manufacturing process.

When applied with voltage supplied to light emitting element 330 and exposed to a high temperature by heat generated by light emitting element 330 combined with the volatile component of the flux filled between land 322a and land 322b, the solder for electrically connecting light emitting element 330 and lands 322a and 322b moves on the land surface or the unit substrate surface. Such movement of the solder causes dendrite, and the generated dendrite causes insulating failure between land 322 and land 322b.

In unit substrate 320 of the illuminating device 3F according to the present embodiment, therefore, hole 324 (slit or depression) for allowing escape of the volatile component of the flux cannot be completely removed in the manufacturing process.

The hole 324 is mainly provided for the purpose of preventing the flux from filling in the space formed by light emitting element 330, and hence the length in the longitudinal direction of hole 324 is preferably up to the extent of a portion that runs out from light emitting element 330 in the top view of unit substrate 320. In other words, a configuration in which the entire hole 324 is not hidden by the light emitting element 330 when seen from the top view of the unit substrate 320 is preferable.

With such a configuration, the flux can sufficiently escape toward the upper surface direction even if the lower surface side of unit substrate 320 is covered with heat dissipating sheet 400 and the like. Hole 324 and the end of unit substrate 320 are preferably arranged with a sufficient spacing to prevent bend of unit substrate 320.

In a typical example, lands 322a and 322b are configured to have a thickness of about 18 μm, and the width d1 in the short direction of hole 324 is formed to about 0.8 mm. Furthermore, the width of the void portion 326 between land 322a and land 322b is about 0.1 mm, and is formed to about 1 mm. A difference d2 between the width d1 of the void portion 326 and the width of the void portion 326 is a gap for preventing the pad formed at the bottom surface of light emitting element 330 from stripping.

The influence of the flux that remained from the mounting process can be reduced by mounting light emitting element 330, and as a result, the reliability of the illuminating device according to the present embodiment can be enhanced.

I. Controller for Lighting

Figure 41:
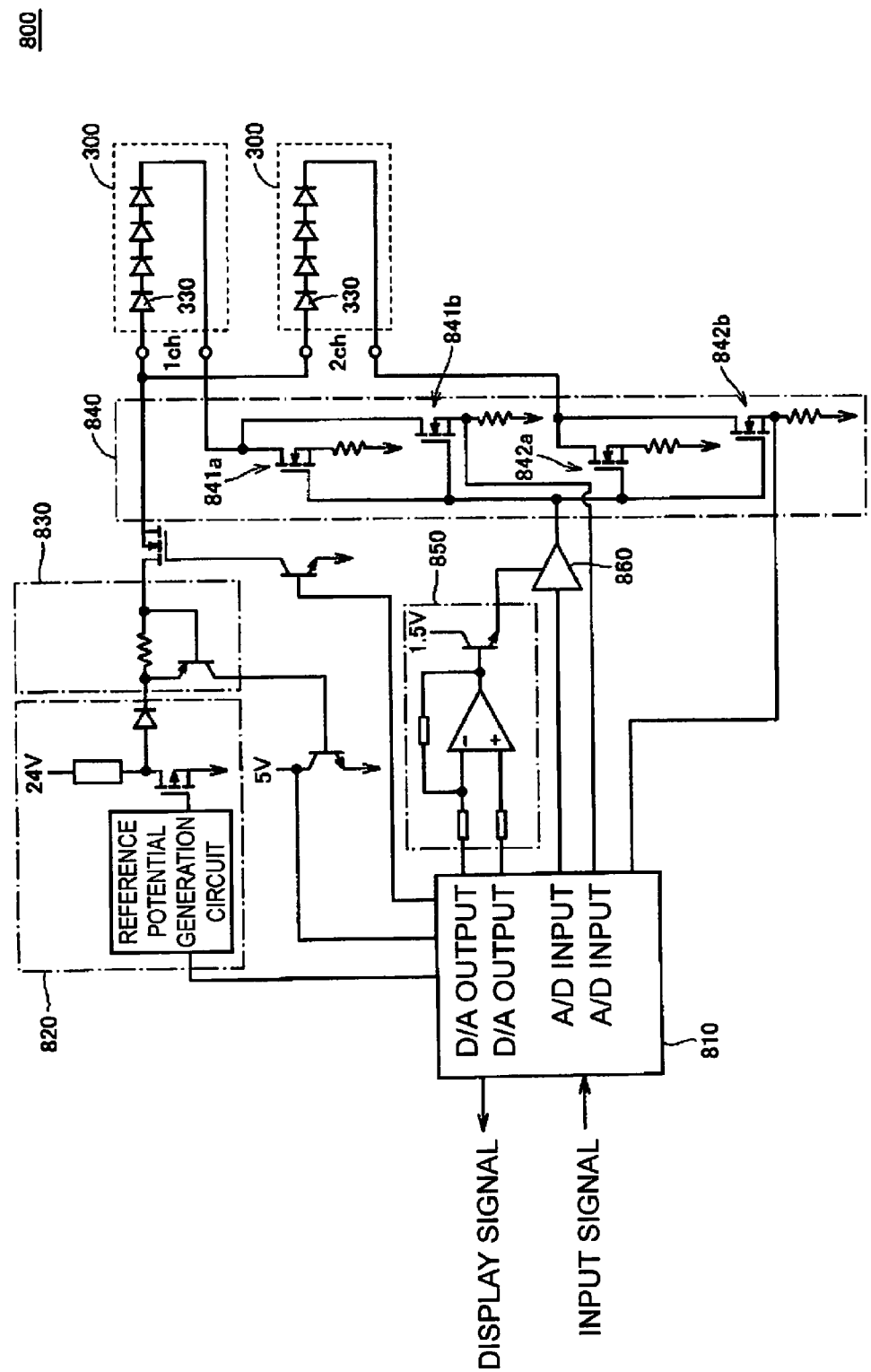
FIG. 41 is a schematic view showing a circuit configuration of a controller for lighting according to the embodiment of the present invention.
Figure 42:
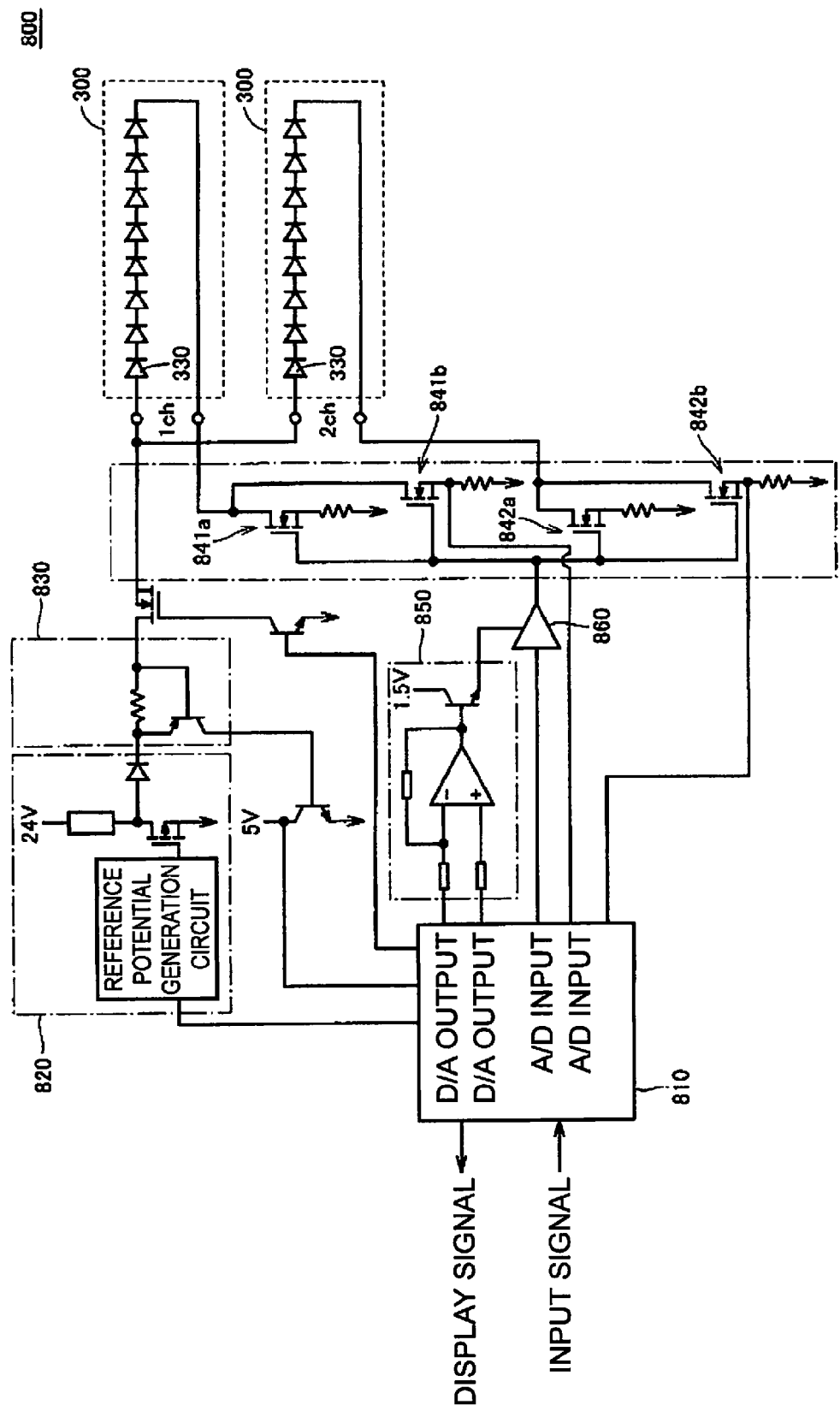
FIG. 42 is a schematic view showing a circuit configuration of a controller for lighting according to the embodiment of the present invention.
Figure 43:
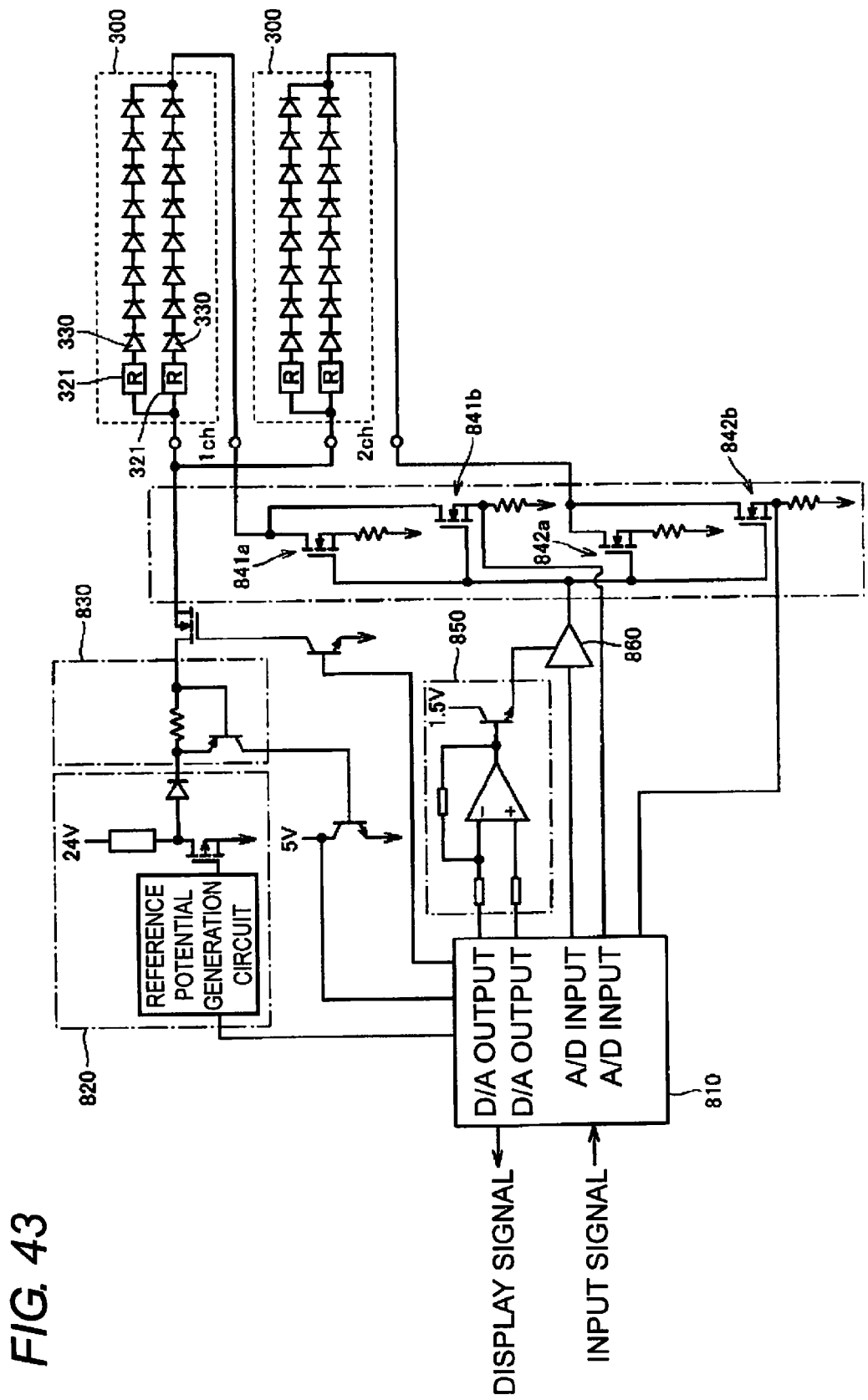
FIG. 43 is a schematic view showing a circuit configuration of a controller for lighting according to the embodiment of the present invention.

The controller (power supply unit) for lighting the illuminating device 3F as described above will now be described. FIGS. 41 to 43 are schematic views showing the circuit configuration of a controller 80 for lighting according to the embodiment of the present invention.

With reference to FIG. 41, the controller 800 includes a control circuit 810, a booster circuit 820, an excess current detection circuit 830, a constant current circuit 840, and a constant voltage circuit 850. The control circuit 810 provides a control signal with respect to each circuit to supply the required current to illuminating device 3F (light emitting element 330) according to the input signal from outside. The control circuit 810 outputs a display signal indicating a current state of the current supply to the outside.

The booster circuit 820 converts the input voltage (24V) to a voltage specified in advance for output. The booster circuit 820 provides a command value corresponding to the voltage to be output from the reference potential generation circuit with respect to a transistor (typically, field effective transistor (FET)) arranged in series between the input node and ground.

The excess current detection circuit 830 is a circuit for limiting the current flowing through the connected light emitting element 330 so as not to become excessively large. Specifically, the excess current detection circuit 830 has a resistor element inserted on the supply path of the current, where a potential difference created when the supply current flows through such a resistor element is provided between the base and the emitter of the transistor. If a voltage exceeding the threshold value defined in advance is generated at both ends of the resistor element, the transistor is in a conduction state and the state change of the transistor is notified to the control circuit 810. The control circuit 810 stops or temporarily shields the current supply by the controller 800 in response to the signal from the excess current detection circuit 830.

The constant current circuit 840 supplies a current of a constant value defined in advance with respect to the connected light emitting element 330. The constant current circuit 840 shown in FIG. 41 enables a power supply of two systems (1 ch and 2 ch). In the constant current circuit 840, the transistors (typically, FET) for controlling current are connected in parallel so that current can be supplied to a greater number of light emitting element 330 group in each system. That is, constant current drivers 841a and 841b are connected in parallel in 1 ch, and constant current drivers 842a and 842b are connected in parallel in 2 ch.

Such a constant current circuit 840 supplies a current value corresponding to the command from the FET driver 860. The power for driving the FET driver 860 is supplied by the constant voltage circuit 850. The constant voltage circuit 850 drops the control voltage (1.5 V) to a specified voltage and outputs to the FET driver 860 according to the command signal from the control circuit 810.

As described above, the controller 800 according to the present embodiment can output the current for driving the light emitting element 330 in two systems. Thus, as shown in FIG. 41, the rigid flexible substrate 300 in which the light emitting element 330 is connected in series by fours can be independently driven. Although it is also dependent on the forward voltage of the light emitting element 330, the light emitting elements 330 can be connected in series by a number not exceeding the voltage value at which the total value of the forward voltage can be output from the controller 800.

For example, FIG. 42 shows an example of driving two rigid flexible substrates 300 in which eight light emitting elements 330 are connected in series, respectively. When simultaneously driving a greater number of light emitting elements 330, a plurality of strings of light emitting elements 330 connected in series by a number smaller than or equal to the upper limit value can be mounted on one rigid flexible substrate 300, as shown in FIG. 43. In such a case, a limiting resistor 321 is preferably inserted to each string to suppress the unbalance of the current flowing through each string.

Therefore, the brightness generated by each light emitting element 330 can be appropriately controlled by connecting a plurality of light emitting elements 330 in series and controlling the magnitude of the current flowing there through. As a result, occurrence of partial brightness non-uniformity etc. can be suppressed even if the ring-shaped illuminating device 3F is configured.

J. Advantage

According to the manufacturing method of the present embodiment, a wide variety of illuminating devices can be manufactured using a substrate having a common pattern. In other words, the illuminating device having an arbitrary size and shape can be realized by cutting the substrate to a substrate piece of a necessary length and forming to a predetermined shape according to the size and the specification of the illuminating device to be manufactured. Thus, a variation (product group) for the illumination field and illumination distance can be accommodated while suppressing the manufacturing cost since a common substrate merely needs to be prepared.

According to the manufacturing method of the present embodiment, the common portion of the substrate piece is formed and the light emitting element is mounted on the individual portion. A physical stress does not generate at the light emitting element since the individual portion where the light emitting element is mounted does not need to be deformed. Thus, the quality of the illuminating device can be enhanced without causing stress to the light emitting element at the time of manufacturing. In other words, the reliability of the illuminating device can be enhanced.

According to the present embodiment, the unit substrate 320 mounted with the lens 200 and the corresponding light emitting element 330 can be positioned and fixed by the holding portion 110 arranged on the base 100 side. The reliability can be enhanced and the optical accuracy can be maintained since the optical component necessary for the irradiation of light can be attached with the housing as the reference.

According to the present embodiment, the lens 200 and the unit substrate 320 are more or less fixed by the holding portion 110 arranged on the base 100 side so that the structure for fixing such optical components from the rear surface side can be simplified. The number of components thus can be reduced and the cost can be reduced, and furthermore, the number of assembly steps can be reduced. The reliability can be enhanced by reducing the number of assembly steps.

According to the present embodiment, the possibility that lens 200 may drop in the direction of the workpiece and the like can be excluded since the holding portion 110 arranged on the base 100 side regulates the movement of the lens 200 in the irradiation surface side. The reliability can be enhanced in regards to such an aspect.

According to the present embodiment, the light emitting element 330 is mounted on the unit substrate 320 configured as an object (rigid body) made from a relatively hard material, and the flexible substrate 340 made from a relatively soft material connected with the unit substrate 320 is concentrically formed, so that the light emitting element 330 can be positioned. Thus, the mechanical stress on the light emitting element 330 can be suppressed.

The embodiments disclosed herein are illustrative in all aspects and should not be construed as being restrictive. The scope of the present invention is defined by the claims rather than by the description made above, and all modifications equivalent in meaning with the claims and within the scope of the invention are to be encompassed herein.

What is claimed is:

1. An illuminating device comprising a substrate mounted with a plurality of light emitting elements, wherein the substrate includes:
   a first flexible portion, made from a first material, having a shape extending in a first direction, and
   a plurality of second portions, made from a second material harder than the first material, each extending in a direction different from the first direction, each second portion being mounted with at least one light emitting element;
   the substrate further includes a wiring for connecting the plurality of light emitting elements over the first portion and the plurality of second portions;
   the first portion is formed in a predefined direction and size according to the illuminating device; and
   each of the second portions is positioned according to an irradiating direction of the light emitting element being mounted,
   wherein the first portion includes a plurality of pads extending in the first direction and being arranged for every predefined interval in the first direction, each second portion is connected to the first portion between two continuous pads included in the first portion and the wiring electrically connects the terminal of the mounted at least one light emitting element to the two corresponding pads.

2. The illuminating device according to claim 1, wherein the first portion is formed in a ring shape along the first direction; and
   each of the second portions is folded in an axial direction perpendicular to the ring defined by the first portion.

3. The illuminating device according to claim 2, wherein the folding is carried out at a connecting portion of the second portion and the first portion.

4. The illuminating device according to claim 1, wherein the second portion is mounted with a chip LED.

5. The illuminating device according to claim 1, wherein the second portion is made of glass epoxy.

6. A method for manufacturing an illuminating device including a light emitting element, comprising:
   a step of creating substrate piece that cuts a substrate mounted with the light emitting element in a first direction, thereby creating a substrate piece, wherein the substrate includes a first flexible portion, and a plurality of second portions that can be bent with respect to the first portion, the first portion includes a plurality of pads extending in a second direction orthogonal to the first direction and being arranged for every predefined interval in the second direction, each second portion is connected to the first portion between two continuous pads included in the first portion and includes wiring for electrically connecting the terminal of the mounted light emitting element to the two corresponding pads, and each second portion is mounted with at least one light emitting element,
   a step of forming the first portion of the substrate piece according to the illuminating device to be manufactured,
   a step of positioning the relative position of the second portion with respect to the formed first portion, and
   a step of forming wiring that supplies power to the pad arranged in the substrate piece.

7. The method of claim 6, wherein the cutting length is changed according to the shape of the illuminating device to be manufactured in the step of creating substrate piece.

8. The method of claim 6, the substrate is cut in the first direction at the position where the pad exists in the step of creating substrate piece.

9. The method of claim 6, wherein the first portion is formed in a ring shape in the forming step.

10. The method of claim 6, wherein first and second portions are both flexible printed substrates.

11. The method of claim 6, wherein the first portion is a flexible printed substrate and the second potion includes a glass epoxy substrate.

12. The method of claim 6, wherein the step of creating substrate piece creates a plurality of substrate pieces.

13. The method of claim 12, wherein the step of forming the first portion forms the first portions of the plurality of created substrate pieces, respectively.

14. The method of claim 13, further comprising a step of fixing the plurality of formed substrate pieces at predefined positional relationship.

15. The method of claim 6, wherein, at the second portion, the wiring is formed so that the plurality of light emitting elements can be mounted in series and wiring for by-passing the light emitting element positioned in the middle when connected in series and the corresponding pad is formed.

16. The method of claim 15, wherein the step of creating substrate piece cuts the substrate in the first direction, cuts one part of the second portion in the substrate piece obtained by cutting in the second direction and connects cut wiring to the corresponding pad.

17. An illuminating device including a light emitting element, comprising:
   a substrate piece on which a light emitting element is mounted and including a pad to be electrically connected with the light emitting element, wherein the substrate piece is obtained by cutting a substrate in a first direction, the substrate including a first flexible portion and a plurality of second portions that can be bent with respect to the first portion, the first portion includes a plurality of pads extending in a second direction orthogonal to the first direction and being arranged for every predefined interval in the second direction, each second portion is connected to the first portion between two continuous pads included in the first portion and includes wiring for electrically connecting the terminal of the mounted light emitting element to the two corresponding pads, each second portion is mounted with at least one light emitting element, the first portion is formed according to the illuminating device, and the second portion is positioned according to the irradiating direction of the light emitting element with respect to the first portion; and
   a circuit for supplying power to the pad.

18. The illuminating device of claim 17, further comprising a unit that changes the relative position of the second portion with respect to the first portion.